US008809046B2

(12) United States Patent
Kilian et al.

(10) Patent No.: US 8,809,046 B2
(45) Date of Patent: Aug. 19, 2014

(54) ALGAL ELONGASES

(75) Inventors: Oliver Kilian, Alameda, CA (US); Bertrand Vick, Berkeley, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 13/459,215

(22) Filed: Apr. 29, 2012

(65) Prior Publication Data
US 2012/0277418 A1 Nov. 1, 2012

Related U.S. Application Data

(60) Provisional application No. 61/480,364, filed on Apr. 28, 2011.

(51) Int. Cl.
C07H 21/04 (2006.01)
C12N 15/00 (2006.01)

(52) U.S. Cl.
USPC ........................ 435/320.1; 536/23.2

(58) Field of Classification Search
None
See application file for complete search history.

(56) References Cited

U.S. PATENT DOCUMENTS

| | | | |
|---|---|---|---|
| 1,926,780 | A | 9/1933 | Lippincott |
| 3,468,057 | A | 9/1969 | Buisson et al. |
| 3,962,466 | A | 6/1976 | Nakabayashi |
| 4,003,337 | A | 1/1977 | Moore |
| 4,267,038 | A | 5/1981 | Thompson |
| 4,365,938 | A | 12/1982 | Warinner |
| 4,535,060 | A | 8/1985 | Comai |
| 4,658,757 | A | 4/1987 | Cook |
| 5,105,085 | A | 4/1992 | McGuire et al. |
| 5,478,208 | A | 12/1995 | Kasai et al. |
| 5,527,456 | A | 6/1996 | Jensen |
| 5,661,017 | A | 8/1997 | Dunahay et al. |
| 5,668,298 | A | 9/1997 | Waldron |
| 5,723,595 | A | 3/1998 | Thompson et al. |
| 5,823,781 | A | 10/1998 | Hitchcock et al. |
| 6,027,900 | A | 2/2000 | Allnutt et al. |
| 6,117,313 | A | 9/2000 | Goldman et al. |
| 6,143,562 | A | 11/2000 | Trulson et al. |
| 6,166,231 | A | 12/2000 | Hoeksema |
| 6,297,054 | B1 | 10/2001 | Maliga et al. |
| 6,372,460 | B1 | 4/2002 | Gladue et al. |
| 6,448,055 | B1 | 9/2002 | Shimizu et al. |
| 6,736,572 | B2 | 5/2004 | Geraghty |
| 6,750,048 | B2 | 6/2004 | Ruecker et al. |
| 6,831,040 | B1 | 12/2004 | Unkefer et al. |
| 6,871,195 | B2 | 3/2005 | Ryan et al. |
| 7,244,609 | B2 | 7/2007 | Drocourt et al. |
| 7,381,326 | B2 | 6/2008 | Haddas |
| 7,410,637 | B2 | 8/2008 | Sayre et al. |
| 7,449,568 | B2 | 11/2008 | Fukuda et al. |
| 7,547,551 | B2 | 6/2009 | Schuler et al. |
| 8,039,230 | B2 | 10/2011 | Otte et al. |
| 8,119,859 | B2 | 2/2012 | Vick et al. |
| 8,314,228 | B2 | 11/2012 | Kilian et al. |
| 8,318,482 | B2 | 11/2012 | Vick et al. |
| 8,440,805 | B2 | 5/2013 | Kilian et al. |
| 2003/0049720 | A1 | 3/2003 | Hoshino et al. |
| 2003/0140021 | A1 | 7/2003 | Ryan et al. |
| 2003/0143743 | A1 | 7/2003 | Schuler et al. |
| 2003/0199490 | A1 | 10/2003 | Antoni-Zimmermann et al. |
| 2003/0211089 | A1 | 11/2003 | Sayre et al. |
| 2004/0161364 | A1 | 8/2004 | Carlson |
| 2004/0262219 | A1 | 12/2004 | Jensen |
| 2005/0064577 | A1 | 3/2005 | Berzin |
| 2005/0095569 | A1 | 5/2005 | Franklin |
| 2005/0124010 | A1 | 6/2005 | Short et al. |
| 2005/0170479 | A1 | 8/2005 | Weaver et al. |
| 2005/0181345 | A1 | 8/2005 | Bradbury et al. |
| 2005/0260553 | A1 | 11/2005 | Berzin |
| 2006/0031087 | A1 | 2/2006 | Fox et al. |
| 2006/0044259 | A1 | 3/2006 | Hotelling et al. |
| 2006/0045750 | A1 | 3/2006 | Stiles |
| 2006/0101535 | A1 | 5/2006 | Forster et al. |
| 2006/0122410 | A1 | 6/2006 | Fichtali et al. |
| 2006/0155558 | A1 | 7/2006 | Corpening |
| 2006/0166243 | A1 | 7/2006 | Su et al. |
| 2006/0166343 | A1 | 7/2006 | Hankamer et al. |
| 2006/0192690 | A1 | 8/2006 | Philipp |
| 2007/0178451 | A1 | 8/2007 | Deng et al. |
| 2008/0118964 | A1 | 5/2008 | Huntley et al. |
| 2008/0120749 | A1 | 5/2008 | Melis et al. |
| 2008/0160488 | A1 | 7/2008 | Younkes et al. |
| 2008/0160591 | A1 | 7/2008 | Willson et al. |
| 2008/0194029 | A1 | 8/2008 | Hegemann et al. |
| 2008/0268539 | A1 * | 10/2008 | Singh et al. ................... 435/419 |
| 2008/0293132 | A1 | 11/2008 | Goldman et al. |
| 2009/0029445 | A1 | 1/2009 | Eckelberry et al. |
| 2009/0061493 | A1 | 3/2009 | Trimbur et al. |

(Continued)

FOREIGN PATENT DOCUMENTS

| CN | 1627764 | 6/2005 |
|---|---|---|
| CN | 1867140 | 11/2006 |

(Continued)

OTHER PUBLICATIONS

IN Journal37/2013 A1, Sep. 13, 2013, Vick et al.
IN Journal31/2013 A1, Aug. 2, 2013, Kilian et al.
Santin-Montanya, I. "Optimal Growth of *Dunaliella primolecta* in Axenic Conditions to Assay Herbicides," Chemosphere, 66, Elsevier 2006, p. 1315-1322.
Felix, R. "Use of the cell wall-less alga *Dunaliella bioculata* in herbicide screening tests," Annals of Applied Biology, 113, 1988, pp. 55-60.
Janssen, M. "Phytosynthetic efficiency of *Dunaliella tertiolecta* under short light/dark cycles," Enzyme and Microbial Technology, 29, 2001, p. 298-305.
Saenz, M.E., "Effects of Technical Grade and a Commercial Formulation of Glyphosate on Algal Population Growth," Bulletin of Environmental Contamination Toxicology, 1997, 59: pp. 638-644.
Christy et al., "Effects of Glyphosate on Growth of *Chlorella*," Weed Science, vol. 29, Issue 1, Jan. 1981, pp. 5-7.

(Continued)

*Primary Examiner* — David J Steadman
*Assistant Examiner* — Paul Holland
(74) *Attorney, Agent, or Firm* — Carr & Ferrell LLP

(57) ABSTRACT

Provided herein are exemplary isolated nucleotide sequences encoding polypeptides having elongase activity, which utilize fatty acids as substrates.

2 Claims, 16 Drawing Sheets

(56) References Cited

U.S. PATENT DOCUMENTS

| | | |
|---|---|---|
| 2009/0061928 A1 | 3/2009 | Lee et al. |
| 2009/0148931 A1 | 6/2009 | Wilkerson et al. |
| 2009/0234146 A1 | 9/2009 | Cooney et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2009/0319338 A1 | 12/2009 | Parks et al. |
| 2009/0325270 A1 | 12/2009 | Vick et al. |
| 2010/0022393 A1 | 1/2010 | Vick |
| 2010/0068772 A1 | 3/2010 | Downey |
| 2010/0100520 A1 | 4/2010 | Dargue et al. |
| 2010/0198659 A1 | 8/2010 | Meltzer et al. |
| 2010/0210003 A1 | 8/2010 | King et al. |
| 2010/0210832 A1 | 8/2010 | Kilian et al. |
| 2010/0314324 A1 | 12/2010 | Rice et al. |
| 2010/0323387 A1 | 12/2010 | Bailey et al. |
| 2010/0330643 A1 | 12/2010 | Kilian et al. |
| 2011/0015415 A1 | 1/2011 | Singh et al. |
| 2011/0059495 A1 | 3/2011 | Bailey et al. |
| 2011/0091977 A1 | 4/2011 | Kilian et al. |
| 2012/0107801 A1 | 5/2012 | Kilian et al. |
| 2012/0190115 A1 | 7/2012 | Kilian et al. |
| 2012/0208279 A1 | 8/2012 | Vick et al. |
| 2012/0277418 A1 | 11/2012 | Kilian et al. |
| 2013/0078716 A1 | 3/2013 | Vick et al. |
| 2013/0102040 A1 | 4/2013 | Radakovits et al. |
| 2013/0131330 A1 | 5/2013 | Kilian et al. |
| 2013/0281683 A1 | 10/2013 | Kilian et al. |
| 2013/0289262 A1 | 10/2013 | Kilian et al. |
| 2013/0295665 A1 | 11/2013 | Kilian et al. |

FOREIGN PATENT DOCUMENTS

| | | |
|---|---|---|
| CN | 1956335 | 5/2007 |
| CN | 101289659 | 10/2008 |
| CN | 102164492 A1 | 8/2011 |
| CN | 102858980 A1 | 1/2013 |
| EP | 2297326 A1 | 3/2011 |
| EP | 2491124 A1 | 8/2012 |
| HK | 1175201 A1 | 6/2013 |
| MX | 20110000934 A1 | 7/2011 |
| WO | WO2004106238 A2 | 12/2004 |
| WO | WO2007084078 A1 | 7/2007 |
| WO | WO2008060571 A2 | 5/2008 |
| WO | WO2008060571 A8 | 5/2008 |
| WO | WO2008106803 A1 | 9/2008 |
| WO | WO2008060571 A3 | 11/2008 |
| WO | WO2009124070 A1 | 10/2009 |
| WO | WO2009149465 A1 | 12/2009 |
| WO | WO2009149470 A1 | 12/2009 |
| WO | WO2010011335 A1 | 1/2010 |
| WO | WO2010147662 A1 | 12/2010 |
| WO | WO2011011463 A2 | 1/2011 |
| WO | WO2011049995 A1 | 4/2011 |
| WO | WO2012149457 A2 | 11/2012 |
| WO | WO2013166065 A1 | 11/2013 |

OTHER PUBLICATIONS

Roessler et al., "Genetic Engineering Approaches for Enhanced Production of Biodiesel Fuel from Microalgae," ACS Symposium Series; American Chemical Society, 1994, pp. 255-270.

Endo et al. "Inactivation of Blasticidin S by *Bacillus cereus* II. Isolation and Characterization of a Plasmid, pBSR 8, from *Bacillus cereus*," The Journal of Antibiotics 41 (2): 271-2589-2601.

Hallmann et al., "Genetic Engineering of the Multicellular Green Alga *Volvox*: A Modified and Multiplied Bacterial Antibiotic Resistance Gene as a Dominant Selectable Marker" The Plant Journal 17(1): 99-109 (Jan. 1999).

Kindle et al. "Stable Nuclear Transformation of *Chlamydomonas* Using the Chlamydomonas Gene for Nitrate Reductase" The Journal of Cell Biology 109 (6, part 1): 2589-2601.

Prein et al. "A Novel Strategy for Constructing N-Terminal Chromosomal Fusions to Green Fluorescent Protein in the Yeast *Saccharomyces cerevisiae*" FEBS Letters 485 (2000) 29-34.

Schiedlmeier et al., "Nuclear Transformation of *Volvox carteri*" Proceedings of the National Academy of Sciences USA 91(11): 5080-5084 (May 1994).

Wendland et al. "PCR-Based Methods Facilitate Targeted Gene Manipulations and Cloning Procedures" Curr.Gen. (2003) 44:115-123.

Molnar et al., "Highly Specific Gene Silencing by Artificial MicroRNAs in the Unicellular Agla *Chlamydomonas reinhardtii*," Plant Jour. ePub Jan. 17, 2009, vol. 58, No. 1, pp. 157-164 (Abstract Only).

Chen et al., "Conditional Production of a Functional Fish Growth Hormone in the Transgenic Line of *Nannochloropsis oculata* (*Eustigmatophyceae*)," J. Phycol. Jun. 2008, vol. 44, No. 3, pp. 768-776.

Nelson et al., "Targeted Disruption of NIT8 Gene in *Chlamydomonas reinhardtii*." Mol. Cell. Bio. Oct. 1995, vol. 15, No. 10, pp. 5762-5769.

Kureshy et al., "Effect of Ozone Treatment on Cultures of *Nannochloropsis oculata, Isochrysis galbana*, and *Chaetoceros gracilis*," Journal of the World Aquaculture Society, 1999, 30(4), pp. 473-480.

Genbank Accession No. U71602 (*Nannochloropsis sp*. Violaxanthing/chlorophyll a binding protein precursor (NANVCP) mRNA, 1998.

Sukenik et al. "Characterization of a Gene Encoding the Light-Harvesting Violaxanthin-Chlorophyll Protein of *Nannochloropsis sp.* (*Eustigmatophyceae*)," Journal of Phycology, Jun. 2000; 36(3), pp. 563-570.

Abe et al., AG610981, *Musmusculus molossinus* DNA, 2004.

Kopczynski et al., CO268749, *Drosophila melanogaster* cDNA clone EK092604, 2004.

Csogor et al., "Light Distribution in a Novel Photobioreactor—Modelling for Optimization," Journal of Applied Phycology, vol. 13, pp. 325-333.

Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.

Zittelli et al., "Mass Cultivation of *Nannochloropsis sp.* in Annular Reactors," Journal of Applied Phycology, vol. 15, pp. 107-113, Mar. 2003.

Strzepek et al., "Photosynthetic Architecture Differs in Coastal and Oceanic Diatoms," Nature, vol. 431, pp. 689-692, Oct. 2004.

Shi et al., "Analysis of Expressed Sequence Tags from the Marine Microalga *Nannochloropsis oculata* (*Eustigmatophyceae*),"Journal of Phycol, vol. 44, pp. 99-102, 2008.

Thiel et al., "Transformation of *Filamentous cyanobacterium* by Electroporation," Journal of Bacteriology, Oct. 1989, vol. 171, No. 10, pp. 5743-5746.

Krienitz et al., "*Nannochloropsis limnetica* (*Eustigmatophyceae*), a new species of picoplankton from freshwater," Phycologica, 2000, vol. 39, No. 3, Abstract.

Lee et al., "Isolation and Characterization of a Xanthophyll Aberrant Mutant of the Green Alga *Nannochloropsis oculata*," Marine Biotechnology, 2006, vol. 8, pp. 238-245.

Sukenik et al., "Regulation of Fatty Acid Composition by Irradiance Level in the *Eustigmatophyte nannochloropsis*," Journal of Phycol., 1989, vol. 25, pp. 686-692.

Rocha et al., "Growth Aspects of the Marine Microalga *Nannochlorpsis gaditana*," Biomolecular Engineering, 2003, vol. 20, pp. 237-242.

Macintyre et al., "Primary Production by Suspended and Benthic Microalgae in a Turbid Estuary: Time-Scales of Variability in San Antonio Bay, Texas," Marine Ecology Progress Series, 1996, vol. 145, pp. 245-268.

Dunahay et al, "Manipulation of Microalgal Lipid Production Using Genetic Engineering," Applied Biochemistry and Biotechnology, 1996, vol. 57/58.

Witkowski et al., "Conversion of a B-Ketoacyl Synthase to a Malonyl Decarboxylase by Replacement of the Active-Site Cysteine with Glutamine," Biochemistry, 1999, vol. 38, 11643-11650.

Kisselev, "Polypeptide Release Factors in Prokaryotes and Eukaryotes: Same Function, Different Structure," Structure, vol. 10, Jan. 2002.

(56) References Cited

OTHER PUBLICATIONS

Whisstock et al., "Predication of protein function from protein sequence and structure," Q. Rev. Biophysics, 2003, vol. 36, pp. 307-340.

Broun et al., "Catalytic Plasticity of Fatty Acid Modification Enzymes Underlying Chemical Diversity of Plant Lipids," Science, vol. 282, 1998.

Wishart et al., "A Single Mutation Converts a Novel Phosphotyrosine Binding Domain into a Dual-specificity Phosphatase," J. Biol. Chem. 1995, vol. 270(45), pp. 26782-26785.

Geng et al, "Construction of a System for the Stable Expression of Foreign Genes in *Dunaliella salina*," Acta Botanica Sinica 46(3): 342-346, 2004.

Chen et al., "Highly Efficient Expression of Rabbit Neutrophil Peptide-1 gene in *Chlorella ellipsoidea* Cells," Current Genetics 39(5-6): 365-370, 2001.

Suga et al., "Control by Osmolarity and Electric Field Strength of Electro-Induced Gene Transfer and Protein Release in Fission Yeast Cells," Journal of Electrostatics 64(12): 796-801, 2006.

International Search Report mailed Sep. 16, 2009 for Application No. PCT/US2009/004296, filed Jul. 24, 2009.

Written Opinion of the International Searching Authority mailed Sep. 16, 2009 for Application No. PCT/US2009/004296, filed Jul. 24, 2009.

Office Action mailed Nov. 14, 2012 in China Patent Application No. 200980138072.X, filed Jul. 24, 2009.

Official Action mailed Jul. 10, 2012 in Mexico Patent Application No. MX/a/2011/000934, filed Jul. 24, 2009.

Official Action mailed Mar. 5, 2013 in Mexico Patent Application No. MX/a/2011/000934, filed Jul. 24, 2009.

Duarte et al., "Glyphosate (GP) Effects with Emphasis on Aquatic Organisms," Colunbia Orinoquia, ISSN: 0121-3709, pp. 70-100, 2004.

Technical Card: Glyphosate, Document filed for the Pesticide Action Network and the Alternatives Thereof, for Latin America (RAP-AL)—Communications and Administration Office, Apr. 2008.

Department of Environment, Housing and Territorial Development Ministry, Resolution (1009), published Jun. 17, 2008.

International Search Report and Written Opinion of the International Searching Authority mailed Oct. 30, 2009 for Application No. PCT/US2009/046656, filed Jun. 8, 2009.

International Search Report and Written Opinion of the International Searching Authority mailed Aug. 12, 2009 for Application No. PCT/US2009/003819, filed Jun. 25 2009.

GenBank Accession No. ER498938 GI: 133929743 May 22, 2007.

Second Office Action mailed Feb. 7, 2014 in Chinese Application No. 201080058106.7 filed Oct. 19, 2010.

International Search Report and Written Opinion of the International Searching Authority mailed Dec. 20, 2010 for Application No. PCT/US2010/053265, filed Oct. 19, 2010.

Extended European Search Report mailed Mar. 19, 2013 in European Patent Application 10825551.4, filed on Oct. 19, 2010.

Minoda et al., "Improvement of Culture Conditions and Evidence for Nuclear Transformation by Homologous Recombination in a Red Alga, *Cyanidioschyzon merolae* 10D," Plant and Cell Physiology, vol. 45, No. 6, Jun. 2004, pp. 667-671.

Hallmann et al., "Gene Replacement by Homologous Recombination in the Multicellular Green Alga, *Volvox carteri*," Proceedings of the National Academy of Sciences in the United States of America, vol. 94, No. 14, 1997, pp. 7469-7474.

Kilian et al., "High-efficiency homologous recombination in the oil-producing alga *Nannochloropsis sp.*," Proceedings of the National Academy of Sciences of the United States of America, vol. 108, No. 52, Dec. 2001, pp. 21265-21269.

Extended European Search Report mailed Oct. 19, 2011 in European Patent Application 09759628.2, filed on Jun. 8, 2009.

Hallmann, "Algal Transgenics and Biotechnology," Transgenic Plant Journal, Global Science Books Ltd., GB, vol. 1, No. 1, Jan. 2007, pp. 81-98.

International Search Report and Written Opinion of the International Searching Authority mailed Oct. 20, 2010 for Application No. PCT/US2010/001754, filed Jun. 16, 2009.

International Search Report and Written Opinion of the International Searching Authority mailed Sep. 9, 2009 for Application No. PCT/US2009/046650, filed Jun. 8, 2009.

International Search Report and Written Opinion of the International Searching Authority mailed Jun. 15, 2011 for Application No. PCT/US2010/042666, filed Jun. 20, 2010.

Pollock, "High Carbon Dioxide Requiring Mutants of *Chlamydomonas reinhardtII*," Created Dec. 2003, [online, retrieved Oct. 14, 2010] <http://etd.lsu.edu/docs/available/etd-0828103-114026/unrestricted/Pollock_dis.pdf>.

Drocourt: GenBank Accession No. X52869.1, created Jan. 3, 1995.

Pan: GenBank Accession No. EE109892.1, created Jun. 23, 2008.

Pan: GenBank Accession No. EE109907, created Jun. 23, 2008.

Henriquez et al.: GenBank Accession No. Q07CY9, created Oct. 31, 2006.

International Search Report and Written Opinion of the International Searching Authority mailed Oct. 16, 2012 for Application No. PCT/US2012/035633, filed Apr. 27, 2012.

Yu et al., "Construction and characterization of a normalized cDNA library of *Nannochloropsis oculata* (*Eustigmatophyceae*)," Chinese Journal of Oceanology and Limnology, vol. 28, No. 4, pp. 802-807, 2010.

Lumbreras et al., "Efficient Foreign Gene Expression in *Chlamydomonas reinhardtii* Mediated by an Endogenous Intron," The Plant Journal, vol. 14, No. 4 Jan. 1, 1998, pp. 441-447, XP001150496, ISN: 0960-7412, DOI:10.1046/j.1365-313X.1998.00145.X.

Rose A.B., "Intron-Mediated Regulation of Gene Expression," Current Topics in Microbiology and Immunology vol. 326, Jan. 1, 2008, pp. 277-290, XP009145370, ISSN: 0070-217X.

Rose A.B., "The Effect of Intron Location on Intron-Mediated Enhancement of Gene Expression in Arabidopsis," The Plant Journal, vol. 40, No. 5, Dec. 1, 2004, pp. 744-751, XP55029911, ISSN: 0960-7412, DOI:10.1111/j.1365-313X.2004.02247.

International Search Report and Written Opinion of the International Searching Authority mailed Sep. 13, 2013 in Application No. PCT/US2013/038939 filed Apr. 30, 2013.

Notice on the First Office Action mailed May 20, 2013 in Chinese Application No. 201080058106.7 filed Oct. 19, 2010.

Examination Report mailed Feb. 20, 2013 in Australian Application No. 2009274500 filed Jul. 24, 2009.

Examination Report mailed Apr. 29, 2013 in European Application No. 09759628.2 filed Jun. 8, 2009.

Examination Report mailed Aug. 29, 2013 in Australian Application No. 2009255947 filed Jun. 8, 2009.

Examination Report mailed Sep. 19, 2013 in Australian Application No. 2010310765 filed Oct. 19, 2010.

Notice on the Second Office Action mailed Sep. 24, 2013 in Chinese Application No. 200980138072.X filed Jul. 24, 2009.

Zuo-Xi Ruan et al., Effects of Acute Glyphosate Exposure on the Growth and Physiology of *Nostoc sphaeroides*, an Edible Cyanobacterium of Paddy Rice Fields, Acta Hydrobiologica Sinica, Jul. 2008 vol. 32, No. 4.

Office Action mailed Nov. 11, 2013 in Mexican Application No. MX/a/2011/000934 filed Jul. 24, 2009.

* cited by examiner

```
ATGACTGCCCAGGGCGTGCCCTTCACCCATCTGGCAGCTTATCCCGGCCCTGTCGCCCTCCTTTATTTCCT
CTATCGCCACACCTGGGTCCCCTCCTGGCCACTGCCCTTACTTCGCCTTCGCCTTCTACACATCCTATGAGAAGCATTTTGATGCCACCGCCTCCTTTATTTCCT
GCCTTTGGAATCGTGTCACTCATAAGTTTGCGGGCGCCGTCCGTGTGGGTACCCATCTCTTGTACCTGCCTCTGTCCCCGTGGGGCGGATTTTCCTTCGAGACACGAT
CTGCGAGTCCCCTGAAGCGACTTACGCGACAACGCCACGGCCTTTGGTGCGTCGTCTTCACTGTTCCAAGCTCCTCGAATTAGTCGACACTATATTGTGGTGTTGCG
GAAGAAGCCTCTCATTTCCTGCATGGTACCACCATGCGACTGTCCTTTGTCCTCATGGTTCGGGCATGTCACGTTCACGCCAGCCCTTATTTCATGGCAATTAATTACT
CGATTCACGGCGTGATGTCATGAGTTCTTTCTAATGCAATTAAAAAGTCCCACAGTGGTTCAATCCTATGTGGCTGACGGTAGCGCAGATCAGCCAAATGTTGTGG
GCATTTGGGTGATTGTATTCGAGTATTGTTGTCAAGTTTTTTGTACAACGATATGCGAAGGAATGCGCCGATTGACGCGAGGGAGGTGGCGGTGGTGGGGAAGG
GTTAATGTATTCGACGATAGGAGTATTGTTCAAGTTTTTTGTACAACGATAAACATCCTTGCTCGAGAGGAAGTGAAAGACGAGTTCGGGTCAAAAAAGAATAA
AGGATAAGGCGACCATGACGGATAGAAGCGGCATATGAGAGCTAAACATCCTTGCTCGAGAGGAAGTGAAAGACGAGTTCGGGTCAAAAAAGAATAA
```

FIG. 1

ATGCCCAAGCTCCAGAAATCTCTAACATCTTCAAATTCTTGAAGGCAGAGACCCTTCCAAGATGCGTCCCCTACAAGAGCATCCCGGACAAAGTGCCCTTCACACAGGTACG
CGTCACCTTCCTCTTTTTCTTCTTGCTACATCAGATCATATTTGTACTATCTACGCTGTCTACTATCGAGGAAAGGCAAATTGTGCGTGCTGTTATACAAGTTTCTCTC
TTCTTCACAACGTTGTGTCCTCATAATGGTACCCTGCCTGATGATATGGTGCAACACGGCCTCGCGCAGGCGGGCAGTTTCTGGTCATTAGCGTTGGCGCTCATCG
CCTTCTGATTCTATTGGAATATTCTCAATTATATAGCACTGGCTTCCCCTGAAAATGAGATGCGAATTTCTTACTGAGTTTATCCCCTTACTCTCCGCACC
TACAGCTCTTTCAGCATTACCCGTCTTAGACCCTTGTATACCCAGTAGACTACTAAAGTCATGGTCTCACGGCCCAAGCACGAGTGGAAGACGGCGTTGGCATGCTGGAACCTGA
CCCTTGCCTTGTGCGGAATGTACGCCTGATGATCATCGTCGGACCTAAAGTCATGGTCTCACGGCCCAAGCACGAGTGGAAGACGGCGTTGGCATGCTGGAACCTGA
TGTTGAGCATTTCTCCTTGTGGGATGATAGGACGGTTCCGCATTGCTGCACAATGTGGCGACGTTGCCCTTAAGGTAGGTACCCCCTGATCCTCTCCTC
CCTCCTCCCTACTCCCTCTACTATGCCCCGTCTGTTGGCGCTGGGCGCTCGTTGGCGCTGGGGCCTCCCGATAGTTACAGCCACATTCACCCGTAATATTCTCTATT
TACTTCTTTTCAATTCTCAGGACACGATCTGTCTTTATCGTCTTGCGCAAAAGCAAGCTGCAGGTATGTATTACTTTATCTCCTATTGTTCGTCTTTCCCCGCCCCTCATTCGTGT
GAGCTAGTAGACACGGTCTTTATCGTCTTTCGCAAAAGCAAGCTGCAGGTATGTATTACTTTATCTCCTATTGTTCGTCTTTCCCCGCCCCTCATTCGTGT
GTGGATGATAATAGATGAAATTCTTGATCAAGACTTTCCAGAAGGCTGGAATTGGAGTCGGCCGTGTGTGATGGATACCATACCGTCTCCTCCTTCGTGGCACTCATAGCGCGTCACCTCA
TCTCCTCCGACCATTCCCATCCATTCGTGAACTAATCCGTGCCATGACCCTCAGTTCCTGCCATCATGTACGCTCATCATCATAAGCTTTCTTTCTCCGTCCCTCCTCTATTAGTTCTTTCCCC
TCCACGGCCTCTACTCGTGGCCATGACATCCGTGCATGACTCCTACTCGTGCATCATCATAAGCTTTCTTTCTCCCCCTCTCCCCTTCCCCCTTCAATCACCTCCCTTAGACTGCCATTAACGCCT
TCAGCTACCGTCTCATACTTTACATAATCCTTGTACTCCCATCATCACCGTCGCGCAGATCTCGCAAATGATCGCAAATGGAAGTTACCTATATGTCGGTGTTGGAATCTGTGCTCCTCTTTTACTTCTGTATACAGACCAGAGC
GGCCTAAGTGCAGGATTCCCCTCCATCAAACACCGTCGCGCAGGGCTCTAATGTATGAAGGTTACCTATATGTCGGTGTTGGAATCTGTGCTCCTCTTTTACTTCTGTATACAGACCAGAGC
ATGCCAGGTGAAGCGTCAAAATGTAACGCAGGGCGTGATGGCCAAGAAATCAAGGCTATGTAA
AAGATTGGGAGGAGGAGAAGAGTGCGGGTGTTGACGATGGCCAAGAAATCAAGGCTATGTAA

FIG. 2

ATGACAACGGCCTTCTTCGAGGTGCTGGGCATGTACGTGCCTTCCGAGAACTACACGGAGCGTGCCGGGAATGAGTTCCACCAAGTCTTCCAAG
GCTTCCCAGCCCTTGCCCCTTTATACATGGACTGGGAGGAAGAATTACAATGCGGAGAAGGTCTTTGGTTCATTATCGACAACTGTGGTTCCCTGGTTCTGCTCT
GCGTGTATTTGCTCTTCATCTTCGGCTACCCGCTGGCCAAACGCTACACATATCGGACACAGATGGCCTGCTGGACACTCGCTCGGAATTCTGCTTGCTTC
ATTAGTTGGATTGGAGCGATGCGGGTGGTACCTCACTCTTTTTCCTGCTCAAGGACGTGGGCTTTGAAGAGGTAGGGGGGAAGGAGGAGGGAGGGGAAAA
AGGGAAGGAGGACGATAGGTGGATAGAGTACTATTTGCTTCAGTTTGGCAGAAAGGTCAGACACTTAAATCCGAAGACGAAGAAGCGATAAAATCTTTAC
AATGCTAAATTGTTTGACGTCTTGGTCATTCAGGCGTTTGTCTTGGATCCAGGCGTGTGGGGCACCGGAGCGCTGTATGGCGA
CGGTGCTGTCGGATTCTGGAGCGTTCTTGAGCAAGGTGCCGAGCTGTCTTTGTGGGTATTGCGGCAAAAGACCCGATCTTCTTGCATT
GGTACGTGCCCTCCTTGTCTCCCCTCTTCTGAGCACCAACCACCGGCGTTTGTCTTGGGTTGCGGGAAAGTCTGAGAATGTCCT
CACATTGGCATGTGGGAGGGGGAAAGAGAAAAGAGAAAAGGAAACTGACGCGGTAAAAGGGACCGGGTAAAGGGGCGGA
GAAACACCAAGGAGAGGTCTTTCTCACTCATTCGTCCCTGCCTATCGACACTCCCCCCCGCATTCCTAGGTACCACCATGTGACCGTGCTGCTCTTCACCTGGTTC
ACGTACTCGAACGAGAACCGGGGATCATCTTATGCCATGAACTACTCGGTGCACGCCGTCATCCCGCCATCGTCAAGCGCGTCCCGA
CTGGTTCCCCACATGGCTCATCACTCTCGCGCAGATCGCACAGATGGTACGTCTCCGCTCTCTCCCTCTCTCGCTCTCCCCACACCTTATTGC
TCAATCGAAGCGCCCTCCAGCGGTGCCGTGCCGCCACGGCAATGTCGAGGACGGTGTCAGTGGGGCGTGTTAGTCATGTGACATGTGACATGTAGGAATACCTTAATG
GCTTCCTTGCTCGGTAGGACTACCCCAAGGGCTCTGTTTGTGCCTTGGACGCGACAAGGGCTCTGGCCTACACAACTACTACCGCGTTCTGCTCACCCCTCCTCCTCTCCCCC
CTTCCCTCCTCTTTCCCTCGCCGCAGCTAGATCGTGGGAGTGTTTGTGCCTACACGCGTTCTCGGGCGGCTCTCGCCGTCTGACGGATCT
GCTGGGCATGCGCGTTGATGTACTCGACGTACCTCTACTTGTTTGCTGCTGCTGCCAGGTACATCCTGGGCAGGGGCAACCGGGCAGGGGCAGTGGCGGGGG
GAAGGGCAAGAAGAAGACCAAGTAG

FIG. 3

ATGTCGGCAATGTCACTACTACCCCGTGGCTATGGCAAGACCCCACCCCTCTTTACAAAACAAGCCAGTATATCACTCGCGACCCCTTGAACC
CGCGGCGGTTCGTGCAAGTATTTCAATCCATCCCAGTCCTTGAACCGCTCTATACCGAGTTTGAGAAAAAATTTAATGTGAAGGAATCGT
ATCGCATCATCCGGGACAACACCTGGCTGCCCATAATTCTGTACCTTCTCTTCATGATCGAAGGCCGAAAAATACGTGGAACG
CCGGAAGCTTGAGGGCAAAGGACCCGTGAATCTGGGACGATTCCCAGCGTTCTGGAATGCTTCCTGGCGTCGTTTCCATTCTAGGTAC
CTTGCGCGTAGTGCCGCATCGTGTTCATGTCACGCATAAGAATTTCAGGGGACGGTTTGCGAGCGCCTGATACGGCGGGTATGG
TGATGGGGCGGGGATGTGGGTGATGCTATTTACGGTTTCCAAGGTCTTGAATTGGTGGACACGATGATCTTGGTGTTGAAGGGGA
AGAATCCTATGTTTCTGCATTGGTGAGGAAGACGTGTGGAGGAGGAGGAGGGATGGGCGGGAAAAGCATTCG
AAATATCACCATACTTATTCCACTCGTCGCTCTCTTCGTCCCGACTCTTCACCACAGTACCACCACGTGACGGTGCTCCTCTACACATGGTT
CTCCTACTCGGCTCGCAATCCCGGCATTTATTTCGTGCACGCCGTCATGTACTCCTACTTCCTGACGGAGA
TCAAGCTCTGCCGAAATGGTTCAAGTATGTGCCCTTCTTTCCCTGTACCCCTTACTCCTCCTTCTCCCTTCATTGCGTCA
TTCATTTCCACACAAGGANNNNNNNNNNagCCCTATGTGATCACCATGGATCACGAGATATCGCAGATGCTTGCCGGGTGTATCACCATCG
CCTCGTTCCTCTACGCCCGTGACCCTTCTGCGGAGTGTTCGGGATATGATTCCCGGTGCGGGATGTACGGACCTACCTGTACTT
CTTCGTCTTGTTTTCATGGAGCGTTTCTGGCCGTCAAGAAGAATGGAAGGAGTTGGGACGGGGGAGAATAATGAGGCAGGAACAGCTCCG
TCGTCATCGTCGTCGTGTCGTCGTCAAGAAGAACAGCCACGAGGGGAGGAGGGGAGGAAAGTCTAGGAAAGAAGAATAG
GCGGGCTGGAGGGGTGGGAAGGGAGGAGACAGCCACGAGGGGAGGAGGAAAGTCTAGGAAAGAAGAATAG

FIG. 4

ATGTCATGGTTTTGGACCCCGCCCCCTCTACGAGACCAGCGAATATGTCACCCGTGATCGTCAACCCCGTCGCTTTGTGCAAGTGTTCCAATCTATCCGGCAC
TCGAACCTCTCTACACCGAGTGGGAAAAGAATTTTAACGTCAAGGAGTCCTACGCCATTATTCGAGACAACTGCTGGTCCCGTCATTGCCGTCATCCTATATCTATC
CTTCCTAGTCGAAGGCAGGAGAACTATGTGGAGCGACGAAAGAAAGCAGGCAAAGGACCGGTTAATCTCGGTCGATTCCGGCAATTGGAATGGGTTCTTGGCCATC
TTCTCGATACTTGGGCGTTGCCGCGTGGTCCCTCATTTCTGTTTTTGTTCACACATAAGGATTTTAAGGAGACGGTTTGTGAGGCTCCGATACGGCGGGGTATGGT
GATGGGGCGGCAGGGATGTGGGTGATGCTGTTTACGGTCTCGAAGGTGTTTGAGTTGATGGATACGGTGATTCTGGTGTTGAAGGGAAAGAACCAATGTTCTTGC
ACTGGTACGTTGGCGCGGAGTGGCGGACGGAAGAAGGGAAACTGACGATGGACAAAGCGAAAGGTCTCGTAGCGACATCAAATCCATCTTCCTGTCGCGACGC
ATGAGGTGCACTCACGCGTGCTCTTGGCACCCGTCCTCCCCTTCCTCCCCTTTCTGTCTCTCTTCACCACAGGTACCACACGTGACAGTGCTCCTCTACACATGGTTC
TCCTACTCGGCCCGCAACCAGCCTATACTTTGTCGCCATGAACTACACACGTGACGCGTCATGTACTTCTTACTACTTCTGTACGGCGCACCCGCCATCTCACTCTTCTCC
GGCTCAGGTACGTCCCCCTTCTCCCCCCCTCCCCCTCCCCCCCCTCCTCCCCCCACTCCCCTCAGCCCCATTTCATCACCCTCAGCCGACCTGGTGTGCCGCCATGTACGCCACCTACCTC
ATCAGAGTCTTCCTTATTCACATTAACGCCGCCTACATCTTCAAGCGACATCTTCGTGGAGCGCTTCTTGGCAGCGCGTCGAGTACGAAGGCAGGGAAGGTACGAAGGAAGAGAAAAGAGGAAGTTAAGGAGGGAATGGGAAGAAGGTGGTGTGA
GTCGGGGTCGGTATCACGCCGCCGCTACATCTTTCAAGCGACATCTTCGTGGAGCGCTTCTTGGCAGCGCGTCGAGTACGAAGG
TATTCTTTGTCGAGTTTTCGTGAGCGCTTCTTGGCAGCGCGTCGAGTACGAAGGCAGGGAAGGTACGAAGGAAGAGAAAAGAGGAAGTTAAGGAGGGAATGGGAAGAAGGTGGTGTGA
ATTGGGACCGCGGCCTTCTCGCTGGTGACTGCCAATGGGAGCGTCGGTGATGGGAATGGGAAGAAGGTGGTGTGA

FIG. 5

ATGGCCGCCGCCCTTCTTGCAGAGACTATCAAAAAACCTGCACGGACTTGTCGCCGCCATTTTAAGTGGGCTGACCCTGCGGGGCGCCATGGTCAAGGCGCCACTCG
CACCTGGCCCTTGGCGGGTTTGACGTGGCCCTGGCTATCGCGGCTTCTCATCATTGTCTCTTTGTGGGTTCGGTACGTCTTTGGAATACGTGTGTATAGAAAG
AGAGATTAGGCGTCGATAAATAGAGTTAGACTGCCTAGGGTATCCAGAGCTGCAACATCTCAGCAGGCGTTCCACCTCTCTTATCCCCTGTTCTCCACCTATCTTCTA
CCTCCCCAAAGGCCATTGATGAAGAACGCAAAGCCAGTAAAATTGTACGGCTTGCAATTCTTCTACAACATCTCCCAGGTGCCCTATGCTCCTATATGTGCATC
GAGGCTGCCATTCAGGCCTCAGGCTAAACGTAGGTCCTCCATCACAGAGTTCCCCTTGTGTTTTAAGTGAAGAAATACAAA
ATAGCAAAACTTACTTTCGCCTCGCTAAAATCTAACAGAACTACACCTTCTGCCGAGCCGTTCAATGCTACCAACATCGCCCCTCTCGTGGCTCTT
CTACGTCTCCAAGGTCTTCGACTTCGCCGACACCGTCTTCATCATCCTGGGAAAGAAGTGGAACCAGTCATCATTTCTGCATGTGTACCACCAGTGACCATCTTTTG
GTGTATTGGTTGAATTTGAATGCGGGATATGATGGCGATCATTCTTAACGGGCAATCCACACGTAATGTACACTTACTACTTCCTCCATGC
ACACCAAGGACATTTGGTGGAAGAAGTACTTGACACTGTTCCAGATTATTCAGTTCCTGACCATGAATGCTCAGGCGATCTACTTGTTATGTGGGTTGCAAGGGGT
TCTCGCCTCAGATTACGAAGCTGTATCTTGGGTACATCCGTCGCTGTTGGTGCTTTTCCTCAATTTTACTTCAAATCGTATTCGGTGTGAAGCCAATGGTAAGAA
GCCGGTTTCCAAGAAGGCTTAA

FIG. 6

```
ATGATTGTTTTCTGCCTCGGATCATGAAAAATCGCCCGGTGAAAGATTTGAGCAAGCCCTTGGCTTTTGGAATTTCTTCCTAGCAGTGTATAGCACCATCGGGGCC
ATTCGTGTCGTCCCTCACTTGTTGTGGTTTATATCCACGCATACTTTAAGGAGACTGTCTGTACCGCCCCTATAGGATCAATGGCGACGGCGCCACTGGTCTGTGG
GTCACGCTCTTCACGCTCTCCAAGGTCGTGGAGTTGGTGGACACCCTCTTTATTTGCTTGAAAGGGAAGAAGCCCATATTCTTGCATTGGTACGTGCTTTAGGTGGGA
AGGGGATACGAGGGACAGGAGCAAGGAATGTGAGAGAGGAATGTGCTCACAATTTCTCTCAATGCATATGAACTACACCTTTCTATTGTCAATA
GGTATCATCATGTTTCCGTCCTCTACTTCACGTGGGCGGCCCACGAGGCTGCCCATGCCCATGGCATGATGTATTTCATGCATGAACTACACCGTGCACTCGGTATGTATTC
CTACTACTTCCTCATGGCCATCCAAGGCTAAGGCTAAGCCCAAGTGGCTCAAGTAAGTACCTCCAGACACCAATTCCTCCCTCAATTCCCTCAATTCTAGCCCGATCTACATCACCTTCATGCAAAT
ATCGGCAACGCGGACTTGAATCTCGCATCTTGTGCATCAATCCAGACACCAATTCCTCCCTCAATTCCCTCAATTCTAGCCCGATCTACATCACCTTCATGCAAAT
TGCGCAAATGATCGTGGGCGTCATCATCACCGCCTTTGGATTTTACTACTCCTCCAAGGATGCTACTTGTGCGGTTGACCCGTTCGTGCTGAAGATCTCGGAGTAAT
TTATGCGTCTTACCTTACTTGTTCATGGAGTTTATGATTAAGCGCTTTTTCGTTGGTGGCGGAGGGGTGGCCGGTGGGAGGGGTGGGAAGAAGGAGGAGGTGCCTCTCCCGAA
AGGCCAAGGGCGAAGAAAGCGCTCTAA
```

FIG. 7

ATGAAGAACAAGAAGAAGCCCTTTGATCTAAAGTGGCCTACTGGAACTGGCTTTGTCCATATTTCGATCATGGGCGTGATTCGCGTGGTGCTCACCTT
GTCTACCTGACAGCGACCAAGGGGTTGAGTGTCGAGCGTGTGCGGGGCCCGAGCCTCTGTATGGCAACGCCGCGGTAGGTTTTGGGTGCAAGCCTTCATTC
TGTCGAAACTGGCAGAGCTGATGACACGGTGTTCATCGTTCTGCGGAAGAAGCCTCACAGTTCTTGCACTGTTGCACTGTTGGGATGGGGTTGGATGGTGGA
GCCAAGGAGAGGGAAAGCGAGTTAGCATTCATGCCGCTGCTATGTGTCCTTACCTGGCGCAGAGCGTTGTGCCCATTACCCATATATAGGGAAAGAAGGAG
GAAAAAGGACACAGAGGGATCCAAACTGTCCTTATGCAGAGATCAATGCCACAAGAGGCATGAACCATAGGAAGTCACGCCCTCCTTTTGTTCGCCCTCCCT
CCTCCCCCTTAGGTACCACCAGTGACGGTCCTCCTGTTCACCTGGTCTCTCTCTCTCTTTCGGTATCATTTTTGTGGCATGAATTATTCGGTGC
ATGCCATTATGTATGGCTACTACTTCCTGGTACGTGATCCCTTCTTCTCCCACTCTATTGTGCACGGTCTCTACCCCTGACATAGATCCTT
TCTCTCTCCCTTCTTGACACTGCCTTCATGCCTCTCCTCTGCTTCTCTCCCTGCTTCGCTCCTGTTATATCCAGGCAACAACT
AAGCCTCTCTGACACTGACCACCTCCCTCCTCCCGCCGACCGCCATTCAGGTCCGACCTTCTGGCTGAAGCCAATCTATC
ACCATGATGCAAATCTCCAAATGGTGGGCGTGCACTGCCGTCTTTTACATCTACAAGATCGGGAGACATGCGCGTGGATCAGGAACTGCT
TATTGCCTGTGGAGTGATGATGTACTCTACCTACCTGTATTTGTTCGTGAGTTTGCGGTAAAGAGGTTCATTTTGCGGTAAAGAGGTTCATTTTGTGAGTTTGCGGTAAAGAGG
GGAAAACGAAGGGCAGTAG

FIG. 8

MTAQGVPFHPIWQLIPALSPFYTSYEKHFDATASFIFLYRHTWVPLLATALYFAFCYYGPKAMRHRKAFD
LKTILCLWNLSLSLIISFAGAVRVGTHLLYLLSPWGGFSFRDTICESPEATYADNATGLWCVVFTVSKLLE
LVDTIFVVLRKKPLIFLHWYHHATVLLCSWFGHVTFTPALYFMAINYSIHGVMYMYFFLMAIKKVPQWFN
PMWLTVAQISQMFVGIWVIVMSCYYKYFEGAQGEGMGKGCAIDGRMIVAICLMYSTYLVLFVKFFVQRYA
GQQKRKGAREVAVVGKEDKATMTDRKRHMELNILASDREEVKDEFRVKKE

FIG. 9

MPKLPEISNIFKFLKADPSKIVPYKSIPDKVPFTQLFQHYPVLDPLYTQYEKNFYASTYVKFAQDTWPVL
PLALCGMYALMIIVGTKVMVSRPKHEWKTALACWNLMLSIFSFCGMIRTVPHLLHNVATLPFKDTICRHP
AETYGEGACGMWVMLFIFSKVPELVDTVFIVFRKSKLQFLHWYHHITVLLFCWHSYAVTSSTGLYFVAMN
YSVHAIMYAYYYLTAINAWPKWIPPSIITVAQISQMIVGVGICASSFYFLYTDPEHCQVKRQNVYAGALM
YGSYLYLFCDFFVRRFLRGGKPRLGEEKSAVLTMAKKIKAM

FIG. 10

MTTAFFEVLGMYVPSENYTERFYTVRGNEFHQVFQGFPALAPLYMDWEKNYNAEKVFWFIIDNSWIPWFS
LCVYLLFIFGYPALAKRYNIGYISARTQMACWNFLLASFSWIGAMRVVPHFFLLKDVGFEEVLCGAPEP
LYGDGAVGFWIQAFVLSKVAELLDTVFVVLRQKDPIFLHWYHHVTVLLFTWFTYSNENPGIIFIAMNYSV
HAVMYTYYWLAIVKRVPDWFPTWLITLAQIAQMIVGVFVAYNYYRVLSSGGSCAVSTDLLWACALMYSTY
LYLFCEFAVRRYILGRGNRAVAAGKGKKKTK

FIG. 11

MSAMSLPPWLWQDPTPLYKTSQYITRDPLNPRRFVQVFQSIPVLEPLYTEFEKKFNVKESYRIIRDNTWL
PIIATILYLSFMIEGRKYVERRKLEGKGPVNLGRFPAFWNAFLASFSILGTLRVVPHLLFMFTHKNFRGT
VCEPPDTAGYGDGAAGMWVMLFTVSKVFELVDTMILVLKGKNPMYHHVTVLLYTWFSYSARNPGIYFVA
MNYSVHAVMYSYYFLTEIKLWPKWFNPMWITMAQISQMLAGVGITIASFLYARDPSCGVVRDMIPWCAG
MYATYLYFFVLFFMERFWPSILNSSSSSSSSSSSSSSSSSSRRKWKELGRGENNEAGTAPAAGG
VGRRTATRGGKSRKEE

FIG. 12

MSWFLDPAPLYETSEYVTRDPVNPVRFVQVFQSIPALEPLYTEWEKNFNVKESYRIIRDNCWVPVIAVIL
YLSFLVEGRNYVERRKKAGKGPVNLGRFPAIWNGFLAIFSILGALRVVPHFLFLFTHKDFKETVCEAPDT
AGYGDGAAGMWVMLFTVSKVFELMDTVILVLKGKNPMFLHWYHHVTVLLYTWFSYSARNPGLYFVAMNYT
VHAVMYSYYFLMEIKLWPKWLSPIFITLMQISQMLVGVGITAAAYIFQRDPSCGVVRDLIPWCAAMYATY
LYFFVEFFVERFLAASSTKAGKEEGKGGKSQLAKKDIGTAAFSLVTANGASVMGNGKKVV

FIG. 13

MAAALLADYQKTCTDLSAAIFKWADPAGAMVKAPTRTWPLAGLDVALAIAAFYLIIVFVGSAMMKNAKPV
KLYGLQFFYNISQVALCSYMCIEAAIQAYRNNYTFLPCEPFNATNPPIAPLLWLFYVSKVFDFADTVFII
LGKKWNQLSFLHVYHHVTIFLVYWLNLNAGYDGDIFLTVILNGAIHTVMYTYFLSMHTKDIWWKKYLTL
FQIIQFLTMNAQAIYLLCVGCKGFSPQITKLYLGYILSLLVLFLNFYFKSYSGVKPNGKKPVSKKA

FIG. 14

MIVFLPRIMKNRPVKDLSKPLAFWNFFLAVYSTIGAIRVVPHLLWFISTHTFKETVCTAPYRINGDGATG
LWVTLFTLSKVVELVDTLFICLKGKPIFLHWYHHVSVLYFTWAAHEAAHAGMYFIGMNYTVHSVMYSYY
FLMAIKAKPKWLNPIYITFMQIAQMIVGVIITAFGFYYSSKDATCAVDPFVLKISGVIYASYLYLFMEFM
IKRFFVGGGGVAGGKKKGGASPRKAKAKKAL

FIG. 15

MKNKKPFDLKWPLAYWNLALSIFSIMGVIRVVPHLVYLTATKGLSVVACGAPEPLYGNAAVGFWVQAFIL
SKLAELIDTVFIVLRKKPLQFLHWYHHVTVLLFTWFCYTKENPGIIFVAMNYSVHAIMYGYYFLMAIQVR
PSWLKPIYITMMQISQMVVGVATAVFYIYKIRSGETCAVDQELLIACGVMYSTYLYLFCEFAVKRFILGG
QGAAGAPKGKTKAQ

FIG. 16

SEQUENCE LISTING

```
<160> NUMBER OF SEQ ID NOS: 16

<210> SEQ ID NO 1
<211> LENGTH: 993
<212> TYPE: DNA
<213> ORGANISM: Nannochloropsis

<400> SEQUENCE: 1
atgactgccc agggcgtgcc ctttcacccc atctggcagc ttatcccggc cctgtcgccc      60
ttctacacat cctatgagaa gcatttgat gccaccgcct cctttatttt cctctatcgc     120
cacacctggg tccctctcct ggccactgcc ctttacttcg ccttttgcta ctacggcccg     180
aaagcgatgc gtcaccgcaa ggcttttgac ctcaagacca ttctctgcct ttggaatctg     240
tcgttgtcac tcataagttt tgcgggcgcc gtccgtgtgg gtaccatct cttgtacctg      300 ctgtccccgt ggggcggatt ttcctttcga dacacgatct gcgagtcccc tgaagcgact     360
tacgccgaca acgccacggg cctttggtgc gtcgtcttca ctgtttccaa gctcctcgaa     420
ttagtcgaca ctatatttgt ggtgttgcgg aagaagcctc tcattttcct gcattggtac     480
caccatgcga ctgtcctttt gtgctcatgg ttcgggcatg tcacgttcac gccagccctt     540
tatttcatgg caattaatta ctcgattcac ggcgtgatgt acatgtactt ctttctaatg     600
gcaattaaaa aagtcccaca gtggttcaat cctatgtggc tgacggtagc gcagatcagc     660
caaatgtttg tgggcatttg ggtgattgtc atgagttgtt actataagta tttcgagggc     720
gctcagggag aaggaatggg gaagggatgc gcgattgacg gccgaatgat tgtggcgatt     780
tgtttaatgt attcgacgta cctagtattg ttcgtcaagt tttttgtaca acgatatgcg     840
ggccaacaaa agcgcaaggg agcgagggag gtggcggtgg tggggaagga ggataaggcg     900
accatgacgg ataggaagcg gcatatggag ctaaacatcc ttgcttcgga tcgagaggaa     960
gtgaaagacg agtttcgggt caaaaaagaa taa                                   993
```

<210> SEQ ID NO 2
<211> LENGTH: 1837
<212> TYPE: DNA
<213> ORGANISM: Nannochloropsis

<400> SEQUENCE: 2

| | |
|---|---|
| atgcccaagc tcccagaaat ctctaacatc ttcaaattct tgaaggcaga cccttccaag | 60 |
| atcgtcccct acaagagcat cccggacaaa gtgcccttca cacaggtacg cgtcaccttc | 120 |
| ctctttttc ttcttgctac atcagatcat atttgtacta tctacgctgt ctactatcga | 180 |
| ggaaagggca aattgtgtgc gtgctgtgta caagtttctc tcttctcttc acaacgttgt | 240 |
| gtcctcataa tggtaccctg cctgatgata tggtgcaaca cacggcctcg cgcaggcggg | 300 |
| cagtttctgg tcattagcgt tggcgctcat cgccttctga ttctattgga ataatagctc | 360 |
| aattatatag catgcactgg cttccccttg aaaatgagat gcgaatttct ttactgagtt | 420 |
| ttatccccctt tactctcccg cacctacagc tctttcagca ttaccccgtc ttagaccccct | 480 |
| tgtataccca gtatgagaag aatttctatg cgagtactta cgtcaaattt gcgcaagaca | 540 |
| cctggccggt ccttcccctt gccttgtgcg gaatgtacgc gctgatgatc atcgtcggca | 600 |
| ctaaagtcat ggtctcacgg cccaagcacg agtggaagac ggcgttggca tgctggaacc | 660 |
| tgatgttgag cattttctcc ttctgtggga tgattaggac ggttccgcat tgctgcaca | 720 |
| atgtggcgac gttgcccttt aaggtaggta ccccctcga tcctctcctc ctcccttcc | 780 |
| tccctcactc cctctctact atgcccccgt cctggcccct ccgttgtcgt ttggcgctgg | 840 |
| ggcctccgat agttacagcc acattcacct gtaatattct cctatttttac ttcttttctc | 900 |
| aattctcagg acacgatctg ccggcacccc gcggaaacgt acggtgaagg ggcctgcggc | 960 |
| atgtgggtga tgctcttcat cttcagcaaa gtccccgagc tagtagacac ggtctttatc | 1020 |
| gtctttcgca aaagcaagct gcaggtatgt atgtattact tttatctcct attgtttctg | 1080 |
| tcttttcttc ccgcccctcca ttcgtcgtgt ggatgtaata gatgaaattc ttgatcaaga | 1140 |
| cttttccagaa ggctcggaat tggagtcggc cgtgtgtgtg gatggatacc ataagaaatt | 1200 |
| aaagagctcc gtctcatctc tcctcccacc attccccatc ccattccgca cccaaccact | 1260 |
| cagttcctgc attggtacca ccacattacc gtcctcctct tctgctggca ctcatacgcc | 1320 |
| gtcacctcct ccaccggcct ctacttcgtg gccatgaact actccgtgca tgccatcatg | 1380 |
| tacgcctact actacctggt acgtgcctta tttctcccgt ccctctatta gtttctttcc | 1440 |
| cctcacgcta ccgtctcata ctttacatat ccttgtactc ccactcataa ggcttttctt | 1500 |
| ttctcctctc ccttccccct tccctaatca cctcccttag actgccatta acgcctggcc | 1560 |
| taagtggatt ccccccctcca tcatcaccgt cgcgcagatc tcgcaaatga tcgtcggtgt | 1620 |
| tggaatctgt gcttcctctt tttacttcct gtatacagac ccagagcatt gccaggtgaa | 1680 |
| gcgtcaaaat gtatacgcag gggctctaat gtatggaagt tacctatatc tgttctgtga | 1740 |
| cttctttgtg cgacgttttt tgagaggagg caagccaaga ttgggagagg agaagagtgc | 1800 |
| ggtgttgacg atggccaaga aaatcaaggc tatgtaa | 1837 |

<210> SEQ ID NO 3
<211> LENGTH: 1736
<212> TYPE: DNA
<213> ORGANISM: Nannochloropsis

<400> SEQUENCE: 3

| | |
|---|---|
| atgacaacgg ccttcttcga ggtgctgggc atgtacgtgc cttccgagaa ctacacggag | 60 |

```
cgtttttaca cggtgcgcgg gaatgagttc caccaagtct tccaaggctt cccagccctt    120
gcccctttat acatggactg ggagaagaat tacaatgcgg agaaggtctt ttggttcatt    180
atcgacaact cgtggattcc ctggttctcg ctctgcgtgt atttgctctt catcttcggc    240
taccccgccc tggccaaacg ctacaatatc ggctacatct ccgctcggac acagatggcc    300
tgctggaatt tcttgcttgc ttcatttagt tggattggag cgatgcgggt ggtacctcac    360
ttttttttcc tgctcaagga cgtgggcttt gaagaggtag ggggggaagg agggagggag    420
gggaaaaagg gaaggaggac gataggtgga tagagtacta ttttgcttct agtttggcag    480
aaaggtcaga cacttaaatc cggaagacga agaagcgata aaattctttt acaatgctaa    540
attgtttgac gtcttggtca ttccttccct ccttctcccc ttcctccctc ctccgctcct    600
ccccaggtgt tgtgcgggc accggagccg ctgtatggcg acggtgctgt cggattctgg    660
atccaggcgt ttgtcttgag caaggtggcc gagctgctgg atacggtctt tgtggtattg    720
cggcaaaaag acccgatctt cttgcattgg tacgtgccct ccttccctcc ctttcctccc    780 tctcccccte cctctttcct gcaccaaccc acggcgtttg cttgtcgttg ggttgcggga    840
aagtctgaga atgtcctcac attggcatgt ggggggggg aaagagagaa aaagagaaag    900
agatcgacgg agggagggaa actggaccgg ctaaaaggga ccgggtaaag ggggcggaga    960
aacaccaagg agaggtcttt ctcactcatt cgtccctgcc tatcgacact ccccccccccg   1020 cattccctag gtaccaccat gtgaccgtgc tgctcttcac ctggttcacg tactcgaacg   1080
agaacccggg gatcatcttc atcgccatga actactcggt gcacgccgtc atgtacacct   1140
actactggct cgccatcgtc aagcgcgtcc ccgactggtt cccccacatgg ctcatcactc   1200 tcgcgcagat cgcacagatg gtacgtctcc cgctccctct ctgcttctct ccctcccttt   1260
cctgctcccc cacaccttat ttgctcaatc gaagcgccct cctcaggcgg tgccgtgcca   1320
cggcaatgtc gaggacggtg tcagtggggc ggtgttagtc atgtatagag ctgtaggaat   1380
accttaatgg cttccttgct cggtaggact accccaaggg ctctgtttgt cgccttggac   1440
gcgacagggg ctctggccta gtgacatgtg ctcacccctc cttccctctc tccccccctt   1500
cctccctctt tccctccgtc gccgcctaga tcgtgggagt gtttgtcgcc tacaactact   1560
accgcgtctt gtcctcgggc ggctcctgcg ccgtctcgac ggatctgctg tgggcatgcg   1620
cgttgatgta ctcgacgtac ctctacttgt tttgtgagtt tgctgtccgc aggtacatcc   1680
tgggcagggg caaccgggca gtggcggcgg ggaagggcaa gaagaagacc aagtag       1736
```

<210> SEQ ID NO 4
<211> LENGTH: 1331
<212> TYPE: DNA
<213> ORGANISM: Nannochloropsis
<220> FEATURE:
<221> NAME/KEY: misc_feature
<222> LOCATION: (924)..(932)
<223> OTHER INFORMATION: n is a, c, g, or t

<400> SEQUENCE: 4

```
atgtcggcaa tgtcactacc cccgtggcta tggcaagacc ccaccctct ttacaaaaca     60 agccagtata tcactcgcga ccccttgaac ccgcggcggt tcgtgcaagt atttcaatcc    120
atcccagtcc ttgaaccgct ctataccgag tttgagaaaa aatttaatgt gaaggaatcg    180
tatcgcatca tccgggacaa cacctggctg cccataattg ccaccattct gtacctctcc    240
ttcatgatcg aaggccgaaa atacgtggaa cgccggaagc ttgagggcaa aggaccccgtg   300
```

```
aatctgggac gattcccagc gttctggaat gctttcctgg cgtcgttttc cattctaggt    360
accttgcgcg tagtgccgca tctgttgttc atgttcacgc ataagaattt caggggacg     420 gtttgcgagc cgcctgatac ggcggggtat ggtgatgggg cggcggggat gtgggtgatg    480
ctatttacgg tttccaaggt cttgaattg gtggacacga tgatcttggt gttgaagggg     540
aagaatccta tgtttctgca ttggtgagga agacgtgtgg gaggagggag ggagggatgg    600
agggatggcg ggcgggaaaa gcattcgaaa tatcaccata cttattccac tcgtcgctct    660
cttcgtcccg actcttcacc acaggtacca ccacgtgacg gtgctcctct acacatggtt    720
ctcctactcg gctcgcaatc ccggcattta tttcgtcgcc atgaactact ccgtgcacgc    780
cgtcatgtac tcctactact tcctgacgga gatcaagctc tggccgaaat ggttcaagta    840
tgtgcccttc tttccctctc gctcttcctt actccctccc tttctccttc ttcccttcat    900
tgcgtcattc atttccacaa ggannnnnnn nnagcccttat gtggatcacc atggcccaaa    960
tatcgcagat gcttgccggg gtcggtatca ccatcgcctc gttcctctac gcccgtgacc   1020
cttcctgcgg agttgttcgg gatatgattc cctggtgcgc ggggatgtac gcgacctacc   1080
tgtacttctt cgtcttgttt ttcatggagc gtttctggcc gtccattttg aattcatcat   1140
catcatcatc atcatcatca tcatcatcat cgtcatcgtc gtcgtcatcg tcgtcgtcgt   1200
cgtcgtcgtc aagaagaaaa tggaaggagt tgggacgggg ggagaataat gaggcaggaa   1260
cagctccggc ggctgagggg gtgggaagga ggacagccac gaggggagga aagtctagga   1320
aagaagaata g                                                        1331

<210> SEQ ID NO 5
<211> LENGTH: 1376
<212> TYPE: DNA
<213> ORGANISM: Nannochloropsis

<400> SEQUENCE: 5
atgtcatggt ttttggaccc cgccccccte tacgagacca gcgaatatgt cacccgtgat     60
cctgtcaacc ccgtccgctt tgtgcaagtg ttccaatcta tcccggcact cgaacctctc    120
tacaccgagt gggaaaagaa ttttaacgtc aaggagtcct accgcattat tcgagacaac    180
tgctgggtcc ctgtcattgc cgtcatccta tatctatcct tcctagtcga aggcaggaac    240
tatgtggagc gacgaaagaa agcaggcaaa ggaccggtta atctcggtcg attcccggca    300
atttggaatg ggttcttggc catcttctcg atacttgggg ctttgcgcgt ggtccctcat    360
ttcctgtttt tgttcacaca taaggatttt aaggagacgg tttgtgaggc tcctgatacg    420
gcggggtatg gtgatggggc ggcagggatg tgggtgatgc tgtttacggt ctcgaaggtg    480
tttgagttga tggatacggt gattctggtg ttgaagggaa agaacccaat gttcttgcac    540
tggtacgttg gcgcggagtg gcggacggaa gaagggaaac tgacgatgga caaagcgaaa    600
ggtctctgta gcgacatcaa atccatcttc ctgtcgcgca cgcatgaggt gcactcacgc    660
gtgcttctgg caccccctctc cctcctttcc tccctttctt gtctctcttc accacaggta    720
ccaccacgtg acagtgctcc tctacacatg gttctcctac tcggcccgca acccaggcct    780
atactttgtc gccatgaact acaccgtgca cgccgtcatg tactcttact acttcctgat    840
ggagatcaag ctctggccga agtggctcag gtacgtcccc ctttcttccc cccctctctc    900
cctccctcct tctcttcctc ctttcctctc ttccatcttc tgtaccgcgc acccgccat    960 ctcactcctt ctctccatca gagtcttcct tattatccac attaacgccc tcctccctct   1020
tcctctcttc cctcccccac tccctcagcc ccattttcat caccctcatg caaatctccc   1080
```

```
aaatgctcgt cggggtcggt atcacggccg ccgcctacat ctttcaacgc gacccttcct    1140
gcggtgttgt gcgcgacctg atcccctggt gtgccgccat gtacgccacc tacctctatt    1200
tctttgtcga gtttttcgtg gagcgcttct tggcagcgtc gagtacgaag cagggaaag     1260 aggaaggtaa gggagggaag agtcaactgg cgaaaaagga tattgggacc gcggccttct    1320
cgctggtgac tgccaatgga gcgtcggtga tggggaatgg gaagaaggtg gtgtga        1376
```

<210> SEQ ID NO 6
<211> LENGTH: 1110
<212> TYPE: DNA
<213> ORGANISM: Nannochloropsis

<400> SEQUENCE: 6

```
atggccgccg cccttcttgc agactatcaa aaaacctgca cggacttgtc cgccgccatt      60
tttaagtggg ctgaccctgc gggcgccatg gtcaaggcgc ccactcgcac ctggcccttg     120
gcgggtttgg acgtggccct ggctatcgcg gctttctacc tcatcattgt ctttgtgggt     180
tcggtacgtc tttggaatac cgtgtgtata aaagagaga ttaggcgtcg ataaatagag      240
ttagactgcg tagggtatcc agagctgcaa catctcagca ggcgcttcca cctctcttat    300
cccctgttct ccacctatct tctacctccc ctccccaaag gccatgatga agaacgcaaa    360
gccagtaaaa ttgtacggct tgcaattctt ctacaacatc tcccaggtcg ccctatgctc    420
ctatatgtgc atcgaggctg ccattcaggc ctaccgtaac gtaggtcctc catccaccct    480
tttcctcctt accatctcca attcccgccc cctcccttg tgttttaagt gaagaaatac     540
aaaatagcaa aacttacttt cgcctctgct aaaatctaac agaactacac cttcctccct    600
tgcgagccgt tcaatgctac caacccacca atcgcccctc tcctgtggct cttctacgtc    660
tccaaggtct tcgacttcgc cgacaccgtc ttcatcatcc tgggaaagaa gtggaaccag    720
ctatcatttc tgcatgtgta ccaccacgtg accatctttt tggtgtattg gttgaatttg    780
aatgcgggat atgatggcga tatttttcctg acagtcattc ttaacggggc aatccacacg    840
gtaatgtaca cttactactt cctctccatg cacaccaagg acatttggtg gaagaagtac    900
ttgacactgt tccagattat tcagttcctg accatgaatg ctcaggcgat ctacttgtta    960
tgtgtgggtt gcaaggggtt ctcgcctcag attacgaagc tgtatcttgg gtacatcctg    1020
tcgctgttgg tgcttttcct caattttac ttcaaatcgt attctggtgt gaagcccaat    1080
ggtaagaagc cggtttccaa gaaggcttaa                                      1110
```

<210> SEQ ID NO 7
<211> LENGTH: 1002
<212> TYPE: DNA
<213> ORGANISM: Nannochloropsis

<400> SEQUENCE: 7

```
atgattgttt tcctgcctcg gatcatgaaa aatcgcccgg tgaaagattt gagcaagccc      60
ttggcttttt ggaatttctt cctagcagtg tatagcacca tcggggccat tcgtgtcgtc    120
cctcacttgt tgtggtttat atccacgcat acttttaagg agactgtctg taccgcccc    180 tataggatca atggcgacgg cgccactggt ctgtgggtca cgctcttcac gctctccaag    240
gtcgtggagt tggtggacac cctctttatt tgcttgaaag ggaagaagcc catattcttg    300
cattggtacg tgctttaggt ggaaggggga tacgagggac aggagcaagg aatgtgagag    360
aaggcgtaaa aagacgcacg tgctcacaat tttcttctca atgcatatgc ataccttct    420
```

```
attgtcaata ggtatcatca tgtttccgtc ctctacttca cgtgggcggc ccacgaggct    480
gcccatgctg gcatgtattt catcggcatg aactacaccg tgcactcggt tatgtattcc    540
tactacttcc tcatggccat caaggctaag cccaagtggc tcaagtaagt acctcccgcc    600
cgttactttt ttaattccat ctcccctctt tcctcccttt tttcttcgct aatcggcaac    660
gcggacttga atctcgcatc ttgtgcatcc aatccagaca ccaattcctc ccttcctccc    720
tccctcaatt ctagcccgat ctacatcacc ttcatgcaaa ttgcgcaaat gatcgtgggc    780
gtcatcatca ccgcctttgg attttactac tcctccaagg atgctacttg tgcggtttga    840
ccgttcgtgc tgaagatctc gggagtaatt tatgcgtctt acctttactt gttcatggag    900
tttatgatta agcgcttttt cgttggtggc ggaggggtgg ccggtgggaa gaagaaggga    960
ggtgcctctc cccgaaaggc caaggcgaag aaagcgctct aa                      1002

<210> SEQ ID NO 8
<211> LENGTH: 1178
<212> TYPE: DNA
<213> ORGANISM: Nannochloropsis

<400> SEQUENCE: 8
atgaagaaca agaagcccct tgatctaaag tggcccttgg cgtactggaa cttggctttg     60
tccatatttt cgatcatggg cgtgattcgc gtggtgcctc accttgtcta cctgacagcg    120 accaagggt tgagtgtcgt ggcgtgcggg gccccggagc tctgtatgg caacgccgcg      180 gtaggttttt gggtgcaagc cttcattctg tcgaaactgg cagagctgat cgacacggtg    240
ttcatcgttc tgcggaagaa gcctctacag ttcttgcact ggtacggggg ttgggatggg    300
ggaatggtgg agccaaggag agggaaagcg agttagcatt catgcgctgc tatgtgtcct    360
ttacctggcg cagagcgttt gtgcccatta cccatatata gggaaagaaa ggaggaaaaa    420
ggacacagag ggatccaaac tgtccttatg cagagatcaa tcgccacaag aggcatgaac    480
cataggaagt cacgccctcc ttttgttcgc ccctccctcc tcctcccctt aggtaccacc    540
acgtgacggt cctcctgttc acctggttct gctacacgaa ggagaatccg ggtatcattt    600 tgtggccat gaattattcg gtgcatgcca ttatgtatgg ctactacttc ctggtacgtg     660 atcccttct ttctctctcc tttctcccac tcctattgtg cacgcgtgtc tctacccct     720 gacatagatc cttttctctc tcccttcttc catgccttca tctctctctt ccttcttctc    780
tactctttct tcccgtcctg tcgcttcctc cttgcttcgc tcctgttata tccaggcaac    840
aactaagcct ctcttgacac tgacccaccc tccctccctc ccgccgccc gaccgccctc    900 ctcagatggc cattcaggtc cgaccttcct ggctgaagcc aatctatatc accatgatgc    960
aaatctccca atggtggtg ggcgtcgcca ctgccgtctt ttacatctac aagatccgat    1020
cgggcgagac atgcgccgtg gatcaggaac tgcttattgc ctgtggagtg atgtactcta    1080
cctacctgta tttgttctgt gagtttgcgg taaagaggtt cattttaggc gggcaggggg    1140 cggcagggc gccgaaggga aaaacgaagg cgcagtag                            1178

<210> SEQ ID NO 9
<211> LENGTH: 330
<212> TYPE: PRT
<213> ORGANISM: Nannochloropsis

<400> SEQUENCE: 9

Met Thr Ala Gln Gly Val Pro Phe His Pro Ile Trp Gln Leu Ile Pro
1               5                   10                  15
```

```
Ala Leu Ser Pro Phe Tyr Thr Ser Tyr Glu Lys His Phe Asp Ala Thr
            20                  25                  30

Ala Ser Phe Ile Phe Leu Tyr Arg His Thr Trp Val Pro Leu Leu Ala
        35                  40                  45

Thr Ala Leu Tyr Phe Ala Phe Cys Tyr Tyr Gly Pro Lys Ala Met Arg
    50                  55                  60

His Arg Lys Ala Phe Asp Leu Lys Thr Ile Leu Cys Leu Trp Asn Leu
65                  70                  75                  80

Ser Leu Ser Leu Ile Ser Phe Ala Gly Ala Val Arg Val Gly Thr His
                85                  90                  95

Leu Leu Tyr Leu Leu Ser Pro Trp Gly Gly Phe Ser Phe Arg Asp Thr
            100                 105                 110

Ile Cys Glu Ser Pro Glu Ala Thr Tyr Ala Asp Asn Ala Thr Gly Leu
        115                 120                 125

Trp Cys Val Phe Thr Val Ser Lys Leu Leu Glu Leu Val Asp Thr
    130                 135                 140

Ile Phe Val Val Leu Arg Lys Pro Leu Ile Phe Leu His Trp Tyr
145                 150                 155                 160

His His Ala Thr Val Leu Leu Cys Ser Trp Phe Gly His Val Thr Phe
                165                 170                 175

Thr Pro Ala Leu Tyr Phe Met Ala Ile Asn Tyr Ser Ile His Gly Val
            180                 185                 190

Met Tyr Met Tyr Phe Phe Leu Met Ala Ile Lys Val Pro Gln Trp
        195                 200                 205

Phe Asn Pro Met Trp Leu Thr Val Ala Gln Ile Ser Gln Met Phe Val
210                 215                 220

Gly Ile Trp Val Ile Val Met Ser Cys Tyr Tyr Lys Tyr Phe Glu Gly
225                 230                 235                 240

Ala Gln Gly Glu Gly Met Gly Lys Gly Cys Ala Ile Asp Gly Arg Met
                245                 250                 255

Ile Val Ala Ile Cys Leu Met Tyr Ser Thr Tyr Leu Val Leu Phe Val
            260                 265                 270

Lys Phe Phe Val Gln Arg Tyr Ala Gly Gln Gln Lys Arg Lys Gly Ala
        275                 280                 285

Arg Glu Val Ala Val Val Gly Lys Glu Asp Lys Ala Thr Met Thr Asp
290                 295                 300

Arg Lys Arg His Met Glu Leu Asn Ile Leu Ala Ser Asp Arg Glu Glu
305                 310                 315                 320

Val Lys Asp Glu Phe Arg Val Lys Lys Glu
                325                 330

<210> SEQ ID NO 10
<211> LENGTH: 321
<212> TYPE: PRT
<213> ORGANISM: Nannochloropsis

<400> SEQUENCE: 10

Met Pro Lys Leu Pro Glu Ile Ser Asn Ile Phe Lys Phe Leu Lys Ala
1               5                   10                  15

Asp Pro Ser Lys Ile Val Pro Tyr Lys Ser Ile Pro Lys Val Pro
            20                  25                  30

Phe Thr Gln Leu Phe Gln His Tyr Pro Val Leu Asp Pro Leu Tyr Thr
        35                  40                  45

Gln Tyr Glu Lys Asn Phe Tyr Ala Ser Thr Tyr Val Lys Phe Ala Gln
    50                  55                  60
```

-continued

Asp Thr Trp Pro Val Leu Pro Leu Ala Leu Cys Gly Met Tyr Ala Leu
65                  70                  75                  80

Met Ile Ile Val Gly Thr Lys Val Met Val Ser Arg Pro Lys His Glu
                85                  90                  95

Trp Lys Thr Ala Leu Ala Cys Trp Asn Leu Met Leu Ser Ile Phe Ser
            100                 105                 110

Phe Cys Gly Met Ile Arg Thr Val Pro His Leu Leu His Asn Val Ala
        115                 120                 125

Thr Leu Pro Phe Lys Asp Thr Ile Cys Arg His Pro Ala Glu Thr Tyr
    130                 135                 140

Gly Glu Gly Ala Cys Gly Met Trp Val Met Leu Phe Ile Phe Ser Lys
145                 150                 155                 160

Val Pro Glu Leu Val Asp Thr Val Phe Ile Val Phe Arg Lys Ser Lys
                165                 170                 175

Leu Gln Phe Leu His Trp Tyr His His Ile Thr Val Leu Leu Phe Cys
            180                 185                 190

Trp His Ser Tyr Ala Val Thr Ser Ser Thr Gly Leu Tyr Phe Val Ala
        195                 200                 205

Met Asn Tyr Ser Val His Ala Ile Met Tyr Ala Tyr Tyr Tyr Leu Thr
    210                 215                 220

Ala Ile Asn Ala Trp Pro Lys Trp Ile Pro Pro Ser Ile Ile Thr Val
225                 230                 235                 240

Ala Gln Ile Ser Gln Met Ile Val Gly Val Gly Ile Cys Ala Ser Ser
                245                 250                 255

Phe Tyr Phe Leu Tyr Thr Asp Pro Glu His Cys Gln Val Lys Arg Gln
            260                 265                 270

Asn Val Tyr Ala Gly Ala Leu Met Tyr Gly Ser Tyr Leu Tyr Leu Phe
        275                 280                 285

Cys Asp Phe Phe Val Arg Arg Phe Leu Arg Gly Gly Lys Pro Arg Leu
    290                 295                 300

Gly Glu Glu Lys Ser Ala Val Leu Thr Met Ala Lys Lys Ile Lys Ala
305                 310                 315                 320

Met

<210> SEQ ID NO 11
<211> LENGTH: 311
<212> TYPE: PRT
<213> ORGANISM: Nannochloropsis

<400> SEQUENCE: 11

Met Thr Thr Ala Phe Phe Glu Val Leu Gly Met Tyr Val Pro Ser Glu
1               5                   10                  15

Asn Tyr Thr Glu Arg Phe Tyr Thr Val Arg Gly Asn Glu Phe His Gln
            20                  25                  30

Val Phe Gln Gly Phe Pro Ala Leu Ala Pro Leu Tyr Met Asp Trp Glu
        35                  40                  45

Lys Asn Tyr Asn Ala Glu Lys Val Phe Trp Phe Ile Ile Asp Asn Ser
    50                  55                  60

Trp Ile Pro Trp Phe Ser Leu Cys Val Tyr Leu Leu Phe Ile Phe Gly
65                  70                  75                  80

Tyr Pro Ala Leu Ala Lys Arg Tyr Asn Ile Gly Tyr Ile Ser Ala Arg
                85                  90                  95

Thr Gln Met Ala Cys Trp Asn Phe Leu Leu Ala Ser Phe Ser Trp Ile
            100                 105                 110

-continued

```
Gly Ala Met Arg Val Val Pro His Phe Phe Leu Leu Lys Asp Val
            115                 120                 125
Gly Phe Glu Glu Val Leu Cys Gly Ala Pro Glu Pro Leu Tyr Gly Asp
130                 135                 140
Gly Ala Val Gly Phe Trp Ile Gln Ala Phe Val Leu Ser Lys Val Ala
145                 150                 155                 160
Glu Leu Leu Asp Thr Val Phe Val Val Leu Arg Gln Lys Asp Pro Ile
                165                 170                 175
Phe Leu His Trp Tyr His His Val Thr Val Leu Leu Phe Thr Trp Phe
            180                 185                 190
Thr Tyr Ser Asn Glu Asn Pro Gly Ile Ile Phe Ile Ala Met Asn Tyr
        195                 200                 205
Ser Val His Ala Val Met Tyr Thr Tyr Tyr Trp Leu Ala Ile Val Lys
    210                 215                 220
Arg Val Pro Asp Trp Phe Pro Thr Trp Leu Ile Thr Leu Ala Gln Ile
225                 230                 235                 240
Ala Gln Met Ile Val Gly Val Phe Val Ala Tyr Asn Tyr Tyr Arg Val
                245                 250                 255
Leu Ser Ser Gly Gly Ser Cys Ala Val Ser Thr Asp Leu Leu Trp Ala
            260                 265                 270
Cys Ala Leu Met Tyr Ser Thr Tyr Leu Tyr Leu Phe Cys Glu Phe Ala
        275                 280                 285
Val Arg Arg Tyr Ile Leu Gly Arg Gly Asn Arg Ala Val Ala Ala Gly
    290                 295                 300
Lys Gly Lys Lys Lys Thr Lys
305                 310

<210> SEQ ID NO 12
<211> LENGTH: 366
<212> TYPE: PRT
<213> ORGANISM: Nannochloropsis

<400> SEQUENCE: 12

Met Ser Ala Met Ser Leu Pro Pro Trp Leu Trp Gln Asp Pro Thr Pro
1               5                   10                  15
Leu Tyr Lys Thr Ser Gln Tyr Ile Thr Arg Asp Pro Leu Asn Pro Arg
            20                  25                  30
Arg Phe Val Gln Val Phe Gln Ser Ile Pro Val Leu Glu Pro Leu Tyr
        35                  40                  45
Thr Glu Phe Glu Lys Lys Phe Asn Val Lys Glu Ser Tyr Arg Ile Ile
    50                  55                  60
Arg Asp Asn Thr Trp Leu Pro Ile Ile Ala Thr Ile Leu Tyr Leu Ser
65                  70                  75                  80
Phe Met Ile Glu Gly Arg Lys Tyr Val Glu Arg Arg Lys Leu Glu Gly
                85                  90                  95
Lys Gly Pro Val Asn Leu Gly Arg Phe Pro Ala Phe Trp Asn Ala Phe
            100                 105                 110
Leu Ala Ser Phe Ser Ile Leu Gly Thr Leu Arg Val Val Pro His Leu
        115                 120                 125
Leu Phe Met Phe Thr His Lys Asn Phe Arg Gly Thr Val Cys Glu Pro
    130                 135                 140
Pro Asp Thr Ala Gly Tyr Gly Asp Gly Ala Ala Gly Met Trp Val Met
145                 150                 155                 160
Leu Phe Thr Val Ser Lys Val Phe Glu Leu Val Asp Thr Met Ile Leu
```

165                 170                 175
Val Leu Lys Gly Lys Asn Pro Met Tyr His Val Thr Val Leu Leu
                180                 185                 190

Tyr Thr Trp Phe Ser Tyr Ser Ala Arg Asn Pro Gly Ile Tyr Phe Val
            195                 200                 205

Ala Met Asn Tyr Ser Val His Ala Val Met Tyr Ser Tyr Tyr Phe Leu
        210                 215                 220

Thr Glu Ile Lys Leu Trp Pro Lys Trp Phe Asn Pro Met Trp Ile Thr
225                 230                 235                 240

Met Ala Gln Ile Ser Gln Met Leu Ala Gly Val Gly Ile Thr Ile Ala
                245                 250                 255

Ser Phe Leu Tyr Ala Arg Asp Pro Ser Cys Gly Val Val Arg Asp Met
            260                 265                 270

Ile Pro Trp Cys Ala Gly Met Tyr Ala Thr Tyr Leu Tyr Phe Phe Val
        275                 280                 285

Leu Phe Phe Met Glu Arg Phe Trp Pro Ser Ile Leu Asn Ser Ser Ser
    290                 295                 300

Ser Ser Ser Ser Ser Ser Ser Ser Ser Ser Ser Ser Ser Ser Ser Ser
305                 310                 315                 320

Ser Ser Ser Ser Ser Ser Arg Arg Lys Trp Lys Glu Leu Gly Arg
                325                 330                 335

Gly Glu Asn Asn Glu Ala Gly Thr Ala Pro Ala Ala Gly Gly Val Gly
                340                 345                 350

Arg Arg Thr Ala Thr Arg Gly Gly Lys Ser Arg Lys Glu Glu
                355                 360                 365

<210> SEQ ID NO 13
<211> LENGTH: 340
<212> TYPE: PRT
<213> ORGANISM: Nannochloropsis

<400> SEQUENCE: 13

Met Ser Trp Phe Leu Asp Pro Ala Pro Leu Tyr Glu Thr Ser Glu Tyr
1               5                   10                  15

Val Thr Arg Asp Pro Val Asn Pro Val Arg Phe Val Gln Val Phe Gln
                20                  25                  30

Ser Ile Pro Ala Leu Glu Pro Leu Tyr Thr Glu Trp Glu Lys Asn Phe
            35                  40                  45

Asn Val Lys Glu Ser Tyr Arg Ile Ile Arg Asp Asn Cys Trp Val Pro
        50                  55                  60

Val Ile Ala Val Ile Leu Tyr Leu Ser Phe Leu Val Glu Gly Arg Asn
65                  70                  75                  80

Tyr Val Glu Arg Arg Lys Lys Ala Gly Lys Gly Pro Val Asn Leu Gly
                85                  90                  95

Arg Phe Pro Ala Ile Trp Asn Gly Phe Leu Ala Ile Phe Ser Ile Leu
            100                 105                 110

Gly Ala Leu Arg Val Val Pro His Phe Leu Phe Leu Phe Thr His Lys
        115                 120                 125

Asp Phe Lys Glu Thr Val Cys Glu Ala Pro Asp Thr Ala Gly Tyr Gly
    130                 135                 140

Asp Gly Ala Ala Gly Met Trp Val Met Leu Phe Thr Val Ser Lys Val
145                 150                 155                 160

Phe Glu Leu Met Asp Thr Val Ile Leu Val Leu Lys Gly Lys Asn Pro
                165                 170                 175

```
Met Phe Leu His Trp Tyr His His Val Thr Val Leu Leu Tyr Thr Trp
            180                 185                 190

Phe Ser Tyr Ser Ala Arg Asn Pro Gly Leu Tyr Phe Val Ala Met Asn
            195                 200                 205

Tyr Thr Val His Ala Val Met Tyr Ser Tyr Tyr Phe Leu Met Glu Ile
            210                 215                 220

Lys Leu Trp Pro Lys Trp Leu Ser Pro Ile Phe Ile Thr Leu Met Gln
225                 230                 235                 240

Ile Ser Gln Met Leu Val Gly Val Gly Ile Thr Ala Ala Ala Tyr Ile
                245                 250                 255

Phe Gln Arg Asp Pro Ser Cys Gly Val Val Arg Asp Leu Ile Pro Trp
            260                 265                 270

Cys Ala Ala Met Tyr Ala Thr Tyr Leu Tyr Phe Phe Val Glu Phe Phe
            275                 280                 285

Val Glu Arg Phe Leu Ala Ala Ser Ser Thr Lys Ala Gly Lys Glu Glu
            290                 295                 300

Gly Lys Gly Gly Lys Ser Gln Leu Ala Lys Lys Asp Ile Gly Thr Ala
305                 310                 315                 320

Ala Phe Ser Leu Val Thr Ala Asn Gly Ala Ser Val Met Gly Asn Gly
                325                 330                 335

Lys Lys Val Val
            340

<210> SEQ ID NO 14
<211> LENGTH: 276
<212> TYPE: PRT
<213> ORGANISM: Nannochloropsis

<400> SEQUENCE: 14

Met Ala Ala Ala Leu Leu Ala Asp Tyr Gln Lys Thr Cys Thr Asp Leu
1               5                   10                  15

Ser Ala Ala Ile Phe Lys Trp Ala Asp Pro Ala Gly Ala Met Val Lys
                20                  25                  30

Ala Pro Thr Arg Thr Trp Pro Leu Ala Gly Leu Asp Val Ala Leu Ala
            35                  40                  45

Ile Ala Ala Phe Tyr Leu Ile Ile Val Phe Val Gly Ser Ala Met Met
        50                  55                  60

Lys Asn Ala Lys Pro Val Lys Leu Tyr Gly Leu Gln Phe Phe Tyr Asn
65                  70                  75                  80

Ile Ser Gln Val Ala Leu Cys Ser Tyr Met Cys Ile Glu Ala Ala Ile
                85                  90                  95

Gln Ala Tyr Arg Asn Asn Tyr Thr Phe Leu Pro Cys Glu Pro Phe Asn
            100                 105                 110

Ala Thr Asn Pro Pro Ile Ala Pro Leu Leu Trp Leu Phe Tyr Val Ser
            115                 120                 125

Lys Val Phe Asp Phe Ala Asp Thr Val Phe Ile Ile Leu Gly Lys Lys
        130                 135                 140

Trp Asn Gln Leu Ser Phe Leu His Val Tyr His His Val Thr Ile Phe
145                 150                 155                 160

Leu Val Tyr Trp Leu Asn Leu Asn Ala Gly Tyr Asp Gly Asp Ile Phe
                165                 170                 175

Leu Thr Val Ile Leu Asn Gly Ala Ile His Thr Val Met Tyr Thr Tyr
            180                 185                 190

Tyr Phe Leu Ser Met His Thr Lys Asp Ile Trp Trp Lys Lys Tyr Leu
            195                 200                 205
```

```
Thr Leu Phe Gln Ile Ile Gln Phe Leu Thr Met Asn Ala Gln Ala Ile
    210                 215                 220

Tyr Leu Leu Cys Val Gly Cys Lys Gly Phe Ser Pro Gln Ile Thr Lys
225                 230                 235                 240

Leu Tyr Leu Gly Tyr Ile Leu Ser Leu Leu Val Leu Phe Leu Asn Phe
                245                 250                 255

Tyr Phe Lys Ser Tyr Ser Gly Val Lys Pro Asn Gly Lys Lys Pro Val
            260                 265                 270

Ser Lys Lys Ala
        275

<210> SEQ ID NO 15
<211> LENGTH: 241
<212> TYPE: PRT
<213> ORGANISM: Nannochloropsis

<400> SEQUENCE: 15

Met Ile Val Phe Leu Pro Arg Ile Met Lys Asn Arg Pro Val Lys Asp
1               5                   10                  15

Leu Ser Lys Pro Leu Ala Phe Trp Asn Phe Leu Ala Val Tyr Ser
            20                  25                  30

Thr Ile Gly Ala Ile Arg Val Val Pro His Leu Leu Trp Phe Ile Ser
        35                  40                  45

Thr His Thr Phe Lys Glu Thr Val Cys Thr Ala Pro Tyr Arg Ile Asn
    50                  55                  60

Gly Asp Gly Ala Thr Gly Leu Trp Val Thr Leu Phe Thr Leu Ser Lys
65                  70                  75                  80

Val Val Glu Leu Val Asp Thr Leu Phe Ile Cys Leu Lys Gly Lys Lys
                85                  90                  95

Pro Ile Phe Leu His Trp Tyr His Val Ser Val Leu Tyr Phe Thr
            100                 105                 110

Trp Ala Ala His Glu Ala Ala His Ala Gly Met Tyr Phe Ile Gly Met
            115                 120                 125

Asn Tyr Thr Val His Ser Val Met Tyr Ser Tyr Tyr Phe Leu Met Ala
130                 135                 140

Ile Lys Ala Lys Pro Lys Trp Leu Asn Pro Ile Tyr Ile Thr Phe Met
145                 150                 155                 160

Gln Ile Ala Gln Met Ile Val Gly Val Ile Ile Thr Ala Phe Gly Phe
                165                 170                 175

Tyr Tyr Ser Ser Lys Asp Ala Thr Cys Ala Val Asp Pro Phe Val Leu
            180                 185                 190

Lys Ile Ser Gly Val Ile Tyr Ala Ser Tyr Leu Tyr Leu Phe Met Glu
        195                 200                 205

Phe Met Ile Lys Arg Phe Phe Val Gly Gly Gly Val Ala Gly Gly
    210                 215                 220

Lys Lys Lys Gly Gly Ala Ser Pro Arg Lys Ala Lys Ala Lys Lys Ala
225                 230                 235                 240

Leu

<210> SEQ ID NO 16
<211> LENGTH: 224
<212> TYPE: PRT
<213> ORGANISM: Nannochloropsis

<400> SEQUENCE: 16
```

-continued

```
Met Lys Asn Lys Lys Pro Phe Asp Leu Lys Trp Pro Leu Ala Tyr Trp
 1               5                  10                 15
Asn Leu Ala Leu Ser Ile Phe Ser Ile Met Gly Val Ile Arg Val Val
            20                  25                  30
Pro His Leu Val Tyr Leu Thr Ala Thr Lys Gly Leu Ser Val Val Ala
            35                  40                  45
Cys Gly Ala Pro Glu Pro Leu Tyr Gly Asn Ala Ala Val Gly Phe Trp
    50                  55                  60
Val Gln Ala Phe Ile Leu Ser Lys Leu Ala Glu Leu Ile Asp Thr Val
 65                 70                  75                  80
Phe Ile Val Leu Arg Lys Lys Pro Leu Gln Phe Leu His Trp Tyr His
                85                  90                  95
His Val Thr Val Leu Leu Phe Thr Trp Phe Cys Tyr Thr Lys Glu Asn
            100                 105                 110
Pro Gly Ile Ile Phe Val Ala Met Asn Tyr Ser Val His Ala Ile Met
            115                 120                 125
Tyr Gly Tyr Tyr Phe Leu Met Ala Ile Gln Val Arg Pro Ser Trp Leu
    130                 135                 140
Lys Pro Ile Tyr Ile Thr Met Met Gln Ile Ser Gln Met Val Val Gly
145                 150                 155                 160
Val Ala Thr Ala Val Phe Tyr Ile Tyr Lys Ile Arg Ser Gly Glu Thr
                165                 170                 175
Cys Ala Val Asp Gln Glu Leu Leu Ile Ala Cys Gly Val Met Tyr Ser
            180                 185                 190
Thr Tyr Leu Tyr Leu Phe Cys Glu Phe Ala Val Lys Arg Phe Ile Leu
            195                 200                 205
Gly Gly Gln Gly Ala Ala Gly Ala Pro Lys Gly Lys Thr Lys Ala Gln
    210                 215                 220
```

ALGAL ELONGASES

CROSS-REFERENCE TO RELATED APPLICATIONS

The present application claims the benefit and priority of U.S. Provisional Patent Application Ser. No. 61/480,364 filed on Apr. 28, 2011, titled "Elongases," which is hereby incorporated by reference.

The present application is related to U.S. Non-Provisional patent application Ser. No. 12/581,812 filed on Oct. 19, 2009, titled "Homologous Recombination in an Algal Nuclear Genome," which is hereby incorporated by reference.

The present application is related to U.S. Non-Provisional patent application Ser. No. 12/480,635 filed on Jun. 8, 2009, titled "VCP-Based Vectors for Algal Cell Transformation," which is hereby incorporated by reference.

The present application is related to U.S. Non-Provisional patent application Ser. No. 12/480,611 filed on Jun. 8, 2009, titled "Transformation of Algal Cells," which is hereby incorporated by reference.

REFERENCE TO SEQUENCE LISTINGS

The present application is filed with sequence listing(s) attached hereto and incorporated by reference.

BACKGROUND OF THE INVENTION

Field of the Invention

This invention relates to molecular biology, and more specifically, to algal elongases.

SUMMARY OF THE INVENTION

Isolated nucleotide sequences encoding polypeptides having elongase activity, which utilize fatty acids as substrates.

BRIEF DESCRIPTION OF THE DRAWINGS

FIG. 1 illustrates the nucleotide sequence encoding elongase 1 (SEQ ID NO:1).
FIG. 2 illustrates the nucleotide sequence encoding elongase 2 (SEQ ID NO:2).
FIG. 3 illustrates the nucleotide sequence encoding elongase 3 (SEQ ID NO:3).
FIG. 4 illustrates the nucleotide sequence encoding elongase 4 (SEQ ID NO:4).
FIG. 5 illustrates the nucleotide sequence encoding elongase 5 (SEQ ID NO:5).
FIG. 6 illustrates the nucleotide sequence encoding elongase 6 (SEQ ID NO:6).
FIG. 7 illustrates the nucleotide sequence encoding elongase 7 (SEQ ID NO:7).
FIG. 8 illustrates the nucleotide sequence encoding elongase 8 (SEQ ID NO:8).
FIG. 9 illustrates the amino acid sequence encoding elongase 1 (SEQ ID NO:9).
FIG. 10 illustrates the amino acid sequence encoding elongase 2 (SEQ ID NO:10).
FIG. 11 illustrates the amino acid sequence encoding elongase 3 (SEQ ID NO:11).
FIG. 12 illustrates the amino acid sequence encoded by elongase 4 (SEQ ID NO:12).
FIG. 13 illustrates the amino acid sequence encoded by elongase 5 (SEQ ID NO:13).
FIG. 14 illustrates the amino acid sequence encoded by elongase 6 (SEQ ID NO:14).
FIG. 15 illustrates the amino acid sequence encoded by elongase 7 (SEQ ID NO:15).
FIG. 16 illustrates the amino acid sequence encoded by elongase 8 (SEQ ID NO:16).

DETAILED DESCRIPTION OF THE INVENTION

A fatty acid is a carboxylic acid with a long aliphatic tail (chain), which is either saturated or unsaturated. Saturated fatty acids are long-chain carboxylic acids that usually have between 12 and 24 carbon atoms and have no double bonds. Unsaturated fatty acids have one or more double bonds between carbon atoms. Most naturally occurring fatty acids have a chain of an even number of carbon atoms, from 4 to 28. Elongases are enzymes which lengthen fatty acids by adding two carbon atoms to a fatty acid's carboxylic acid end.

Provided herein are isolated nucleotide sequences encoding polypeptides having elongase activity, which utilize fatty acids as substrates.

The inventors sequenced the entire genome of algal genus Nannochloropsis and identified genes involved in fatty acid metabolism. They identified various elongases, including exemplary elongases which they designated as elongases 1-9.

The inventors manipulated the activities of the above-specified exemplary elongase genes by:
1. Overexpression of the subject elongase gene with a strong promoter.
2. Promoter replacement or promoter insertion in front of the subject elongase gene within the genome via homologous recombination.
3. Knock out of the subject elongase gene via insertion of a transformation construct into the gene or replacement of a part of or the entire subject elongase gene via homologous recombination.

Exemplary support for the above-mentioned methods may be found in U.S. Non-Provisional Patent Application Ser. No. 12/581,812 filed on Oct. 19, 2009, titled "Homologous Recombination in an Algal Nuclear Genome," U.S. Non-Provisional Patent Application Ser. No. 12/480,635 filed on Jun. 8, 2009, titled "VCP-Based Vectors for Algal Cell Transformation," and U.S. Non-Provisional Patent Application Ser. No. 12/480,611 filed on Jun. 8, 2009, titled "Transformation of Algal Cells," all of which are hereby incorporated by reference.

A transformation construct or vector may comprise any number of promoters, genes, and/or other nucleic acid polymers (naturally occurring or synthetic) and/or their analogs, or other compounds that do not interfere with the ability of the transformation construct to enter the algal cell or the algal genome, or to function. In some embodiments, additional nucleotides may appear in the transformation construct to facilitate or direct the insertion of the construct (or any part thereof) into a desired location in the genome.

Accordingly, the inventors were able to manipulate the activities of the various exemplary elongases for the purpose of modifying the contents of certain fatty acids within algal genus Nannochloropsis.

Some of these elongases, i.e. Elongases 6-8, are down-regulated under conditions when poly unsaturated fatty acid ("PUFA") biosynthesis is down-regulated as well (i.e. during Nitrogen starvation). These genes are excellent targets for over-expression, in order to achieve elevated PUFA biosynthesis. Down-regulation of these (or other) genes, as an example, by replacement of the endogenous promoter or insertion of a weaker promoter in front of the respective elongase gene could lead to a higher content of short chain fatty acids. Down-regulation of transcription could also be achieved, in some cases, by insertion of a commonly strong promoter in front of the respective elongase gene, presumably by modifying the respective chromatin arrangement around the said elongase gene, thus leading to a lower transcription level. Also, the introduction of point mutations into the gene when inserting another promoter in front of such a gene via the homologous recombination flanks utilized, could lead to an altered activity of the respective gene products.

Over expression and knock out mutants of said elongase genes suggest that at least 4 elongases with overlapping functions are operating in the biosynthesis pathway leading to Eicosapentaenoic acid ("EPA"): these are, but not limited to: Elongases 5, 6, 7, and 9. Transcriptome analysis also suggests that Elongase 8 is operating as well in the fatty acid biosynthesis pathway to EPA.

FIG. 1 illustrates the nucleotide sequence encoding elongase 1 (SEQ ID NO:1).

FIG. 2 illustrates the nucleotide sequence encoding elongase 2 (SEQ ID NO:2).

FIG. 3 illustrates the nucleotide sequence encoding elongase 3 (SEQ ID NO:3).

FIG. 4 illustrates the nucleotide sequence encoding elongase 4 (SEQ ID NO:4).

FIG. 5 illustrates the nucleotide sequence encoding elongase 5 (SEQ ID NO:5).

FIG. 6 illustrates the nucleotide sequence encoding elongase 6 (SEQ ID NO:6).

FIG. 7 illustrates the nucleotide sequence encoding elongase 7 (SEQ ID NO:7).

FIG. 8 illustrates the nucleotide sequence encoding elongase 8 (SEQ ID NO:8).

FIG. 9 illustrates the amino acid sequence encoding elongase 1 (SEQ ID NO:9).

FIG. 10 illustrates the amino acid sequence encoding elongase 2 (SEQ ID NO:10).

FIG. 11 illustrates the amino acid sequence encoding elongase 3 (SEQ ID NO:11).

FIG. 12 illustrates the amino acid sequence encoded by elongase 4 (SEQ ID NO:12).

FIG. 13 illustrates the amino acid sequence encoded by elongase 5 (SEQ ID NO:13).

FIG. 14 illustrates the amino acid sequence encoded by elongase 6 (SEQ ID NO:14).

FIG. 15 illustrates the amino acid sequence encoded by elongase 7 (SEQ ID NO:15).

FIG. 16 illustrates the amino acid sequence encoded by elongase 8 (SEQ ID NO:16).

While various embodiments have been described above, it should be understood that they have been presented by way of example only, and not limitation. Thus, the breadth and scope of a preferred embodiment should not be limited by any of the above-described exemplary embodiments.

What is claimed is:

1. A transformation vector comprising an isolated nucleic acid encoding a polypeptide having elongase activity, wherein the isolated nucleic acid comprises the nucleotide sequence set forth in SEQ ID NO:1.

2. The transformation vector of claim 1, wherein the polypeptide comprises the amino acid sequence set forth in of SEQ ID NO:9.

* * * * *